(12) United States Patent
Sim et al.

(10) Patent No.: US 9,764,066 B2
(45) Date of Patent: *Sep. 19, 2017

(54) COMPOSITE LACRIMAL INSERT AND RELATED METHODS

(71) Applicant: Mati Therapeutics Inc., Austin, TX (US)

(72) Inventors: Sylvie Sim, Mountain View, CA (US); Rachna Jain, Milpitas, CA (US); Kathleen Farinas, Los Altos, CA (US)

(73) Assignee: Mati Therapeutics Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/831,965

(22) Filed: Aug. 21, 2015

(65) Prior Publication Data

US 2015/0367037 A1   Dec. 24, 2015

Related U.S. Application Data

(63) Continuation of application No. 12/432,553, filed on Apr. 29, 2009, now Pat. No. 9,132,088.

(60) Provisional application No. 61/049,337, filed on Apr. 30, 2008.

(51) Int. Cl.
| | |
|---|---|
| *A61L 31/06* | (2006.01) |
| *A61F 9/00* | (2006.01) |
| *A61K 9/00* | (2006.01) |
| *A61K 47/34* | (2017.01) |
| *A61L 31/14* | (2006.01) |
| *A61L 31/16* | (2006.01) |

(52) U.S. Cl.
CPC ............ *A61L 31/06* (2013.01); *A61F 9/0008* (2013.01); *A61F 9/0017* (2013.01); *A61K 9/0051* (2013.01); *A61K 47/34* (2013.01); *A61L 31/145* (2013.01); *A61L 31/16* (2013.01)

(58) Field of Classification Search
CPC ..... A61F 9/0008; A61F 9/0017; A61K 47/34; A61K 9/0051; A61L 31/145; A61L 31/16
See application file for complete search history.

(56) References Cited

U.S. PATENT DOCUMENTS

| | | |
|---|---|---|
| 3,865,108 A | 2/1975 | Hartop |
| 3,949,750 A | 4/1976 | Freeman |
| 4,014,335 A | 3/1977 | Arnold |
| 4,281,654 A | 8/1981 | Shell |
| 4,660,546 A | 4/1987 | Herrick |
| 4,886,488 A | 12/1989 | White |
| 4,915,684 A | 4/1990 | MacKeen |
| 4,959,048 A | 9/1990 | Seder |
| 5,041,081 A | 8/1991 | Odrich |
| 5,049,142 A | 9/1991 | Herrick |
| 5,053,030 A | 10/1991 | Herrick |
| 5,098,443 A | 3/1992 | Parel |
| 5,128,058 A | 7/1992 | Ishii |
| 5,133,159 A | 7/1992 | Nelson |
| 5,163,959 A | 11/1992 | Herrick |
| 5,171,270 A | 12/1992 | Herrick |
| 5,283,063 A | 2/1994 | Freeman |
| 5,318,513 A | 6/1994 | Leib |
| 5,334,137 A | 8/1994 | Freeman |
| 5,395,618 A | 3/1995 | Darougar |
| 5,417,651 A | 5/1995 | Guena |
| 5,423,777 A | 6/1995 | Tajiri |
| 5,466,233 A | 11/1995 | Weiner |
| 5,556,633 A | 9/1996 | Haddad |
| 5,707,643 A | 1/1998 | Ogura |
| 5,723,005 A | 3/1998 | Herrick |
| 5,766,243 A | 6/1998 | Christensen |
| 5,770,589 A | 6/1998 | Billson |
| 5,773,019 A | 6/1998 | Ashton |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano |
| 5,961,370 A | 10/1999 | Valle |
| 5,962,383 A | 10/1999 | Doyel |
| 5,993,407 A | 11/1999 | Moazed |
| 6,010,391 A | 1/2000 | Lewellen |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson |
| 6,149,684 A | 11/2000 | Herrick |
| 6,196,993 B1 | 3/2001 | Cohan |

(Continued)

FOREIGN PATENT DOCUMENTS

| | | |
|---|---|---|
| AU | 20023644336 | 7/2003 |
| EP | 0442745 A1 | 8/1991 |
| EP | 0621022 | 7/1999 |
| JP | 10033584 | 2/1998 |
| JP | 2004202276 A | 7/2004 |
| JP | 2005000628 A | 1/2005 |
| JP | 2005058622 A | 3/2005 |
| JP | 2005110765 A | 4/2005 |
| JP | 2005110930 A | 4/2005 |
| JP | 2005312835 A | 11/2005 |
| JP | 2005319190 A | 11/2005 |
| JP | 2005328922 A | 12/2005 |
| JP | 2007195819 A | 8/2007 |

(Continued)

OTHER PUBLICATIONS

"U.S. Appl. No. 10/825,047, Preliminary Amendment and Response filed Aug. 18, 2008 to Restriction Requirement dated Jul. 17, 2008", 10 pgs.

(Continued)

*Primary Examiner* — Mark V Stevens
(74) *Attorney, Agent, or Firm* — Mati Therapeutics Inc.; Koren Anderson

(57) ABSTRACT

Lacrimal implants, methods of making lacrimal implants, and methods of treating ocular, respiration or other diseases or disorders using lacrimal implants are disclosed.

19 Claims, 14 Drawing Sheets

(56) References Cited

U.S. PATENT DOCUMENTS

| | | |
|---|---|---|
| 6,234,175 B1 | 5/2001 | Zhou |
| 6,238,363 B1 | 5/2001 | Kurihashi |
| 6,254,562 B1 | 7/2001 | Fouere |
| 6,264,971 B1 | 7/2001 | Darougar |
| 6,290,684 B1 | 9/2001 | Herrick |
| 6,306,114 B1 | 10/2001 | Freeman |
| 6,331,313 B1 | 12/2001 | Wong |
| 6,371,122 B1 | 4/2002 | Mandelkorn |
| 6,375,972 B1 | 4/2002 | Guo |
| 6,383,192 B1 | 5/2002 | Kurihashi |
| 6,428,502 B1 | 8/2002 | Lang |
| 6,455,062 B1 | 9/2002 | Olejnik |
| 6,605,108 B2 | 8/2003 | Mendius |
| 6,629,533 B1 | 10/2003 | Webb |
| 6,706,275 B1 | 3/2004 | Camp |
| 6,729,939 B2 | 5/2004 | Wrue |
| 6,756,049 B2 | 6/2004 | Brubaker |
| 6,780,164 B2 | 8/2004 | Bergheim |
| 6,840,931 B2 | 1/2005 | Peterson |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker |
| 6,994,684 B2 | 2/2006 | Murray |
| 7,017,580 B2 | 3/2006 | Prescott |
| 7,117,870 B2 | 10/2006 | Prescott |
| 7,135,009 B2 | 11/2006 | Tu |
| 7,204,253 B2 | 4/2007 | Mendius |
| 7,204,995 B2 | 4/2007 | El-Sherif |
| 7,244,444 B2 | 7/2007 | Bates |
| 9,132,088 B2 * | 9/2015 | Sim ............ A61K 9/0051 |
| 2002/0032400 A1 | 3/2002 | Moazed |
| 2002/0055701 A1 | 5/2002 | Fischell |
| 2002/0151960 A1 | 10/2002 | Mendius |
| 2002/0198453 A1 | 12/2002 | Herrick |
| 2003/0130612 A1 | 7/2003 | Moazed |
| 2004/0102729 A1 | 5/2004 | Haffner |
| 2004/0121014 A1 | 6/2004 | Guo |
| 2004/0127843 A1 | 7/2004 | Tu |
| 2004/0137068 A1 | 7/2004 | Bhushan |
| 2004/0141151 A1 | 7/2004 | Gillespie |
| 2004/0147870 A1 | 7/2004 | Burns |
| 2004/0170685 A1 | 9/2004 | Carpenter |
| 2004/0175410 A1 | 9/2004 | Ashton |
| 2004/0210182 A1 | 10/2004 | Fouere |
| 2004/0249333 A1 | 12/2004 | Bergheim |
| 2004/0265356 A1 | 12/2004 | Mosack |
| 2005/0048121 A1 | 3/2005 | East |
| 2005/0095269 A1 | 5/2005 | Ainpour |
| 2005/0129731 A1 | 6/2005 | Horres |
| 2005/0197614 A1 | 9/2005 | Pritchard |
| 2005/0220882 A1 | 10/2005 | Pritchard |
| 2005/0232972 A1 | 10/2005 | Odrich |
| 2005/0244469 A1 | 11/2005 | Whitcup |
| 2005/0266047 A1 | 12/2005 | Tu |
| 2005/0271704 A1 | 12/2005 | Tu |
| 2005/0283109 A1 | 12/2005 | Peyman |
| 2006/0013835 A1 | 1/2006 | Anderson |
| 2006/0020248 A1 | 1/2006 | Prescott |
| 2006/0020253 A1 | 1/2006 | Prescott |
| 2006/0074370 A1 | 4/2006 | Zhou |
| 2006/0100700 A1 | 5/2006 | Bernard |
| 2006/0106352 A1 | 5/2006 | Kurihashi |
| 2006/0122553 A1 | 6/2006 | Hanna |
| 2007/0083146 A1 | 4/2007 | Murray |
| 2007/0123924 A1 | 5/2007 | Becker |
| 2007/0132125 A1 | 6/2007 | Rastogi |
| 2007/0135914 A1 | 6/2007 | Herrick |
| 2007/0243230 A1 | 10/2007 | de Juan |
| 2007/0269487 A1 | 11/2007 | de Juan |
| 2007/0298075 A1 | 12/2007 | Borgia |
| 2007/0299515 A1 | 12/2007 | Herrick |
| 2007/0299516 A1 | 12/2007 | Cui |
| 2008/0038317 A1 | 2/2008 | Chang |
| 2008/0045878 A1 | 2/2008 | Bergheim |
| 2008/0045911 A1 | 2/2008 | Borgia |
| 2008/0181930 A1 | 7/2008 | Rodstrom |
| 2009/0092654 A1 | 4/2009 | de Juan |
| 2009/0104243 A1 | 4/2009 | Utkhede |
| 2009/0104248 A1 | 4/2009 | Rapacki |
| 2009/0105749 A1 | 4/2009 | de Juan |
| 2009/0118702 A1 | 5/2009 | Lazar |
| 2009/0264861 A1 | 10/2009 | Jain |
| 2010/0274224 A1 | 10/2010 | Jain |

FOREIGN PATENT DOCUMENTS

| | | |
|---|---|---|
| WO | WO-9833461 | 8/1998 |
| WO | WO-9842282 | 10/1998 |
| WO | WO-9937260 | 7/1999 |
| WO | WO-9944553 | 9/1999 |
| WO | WO-9964089 | 12/1999 |
| WO | WO-9965544 | 12/1999 |
| WO | WO-0027321 | 5/2000 |
| WO | WO-0062760 | 10/2000 |
| WO | WO-0211783 | 2/2002 |
| WO | WO-02058667 | 8/2002 |
| WO | WO-02083198 | 10/2002 |
| WO | WO-03017897 | 3/2003 |
| WO | WO-03022242 | 3/2003 |
| WO | WO-03057101 | 7/2003 |
| WO | WO-2004004614 | 1/2004 |
| WO | WO-2004024043 | 3/2004 |
| WO | WO-2004105658 | 12/2004 |
| WO | WO-2004112639 | 12/2004 |
| WO | WO-2005000154 | 1/2005 |
| WO | WO-2005086694 | 9/2005 |
| WO | WO-2006014434 | 2/2006 |
| WO | WO-2006031658 | 3/2006 |
| WO | WO-2006037321 | 4/2006 |
| WO | WO-2006044669 | 4/2006 |
| WO | WO-2006057859 | 6/2006 |
| WO | WO-2006096586 | 9/2006 |
| WO | WO-2007008262 | 1/2007 |
| WO | WO-2007115259 | 10/2007 |
| WO | WO-2007115261 | 10/2007 |
| WO | WO-2007149771 | 12/2007 |
| WO | WO-2007149773 | 12/2007 |
| WO | WO-2007149832 | 12/2007 |
| WO | WO-2008056060 | 5/2008 |
| WO | WO-2008094989 | 8/2008 |
| WO | WO-2009032328 | 3/2009 |
| WO | WO-2009035562 | 3/2009 |
| WO | WO-2009105178 | 8/2009 |

OTHER PUBLICATIONS

"U.S. Appl. No. 10/825,047, Response filed Apr. 22, 2009 to Non Final Office Action dated Oct. 22, 2008", 17 pgs.

"U.S. Appl. No. 10/825,047, Final Office Action dated Jun. 9, 2009", 14 pgs.

"U.S. Appl. No. 10/825,047, Non-Final Office Action dated Oct. 22, 2008", 13 pgs.

"U.S. Appl. No. 10/825,047, Restriction Requirement dated Jul. 17, 2008", 6 pgs.

"U.S. Appl. No. 11/695,537, Notice dated Nov. 28, 2008 Regarding a Noncompliant or Nonresponsive Amendment filed on Nov. 3, 2008", 3 pgs.

"U.S. Appl. No. 11/695,537, Response filed Nov. 3, 2008 to Restriction Requirement dated Oct. 3, 2008", 15 pgs.

"U.S. Appl. No. 11/695,537, Response filed Dec. 17, 2008 to Office Communication dated Nov. 28, 2008", 8 pgs.

"U.S. Appl. No. 11/695,537, Restriction Requirement dated Oct. 3, 2008", 10 pgs.

"U.S. Appl. No. 11/695,545, Preliminary Amendment and Response filed Nov. 6, 2008 to Restriction Requirement dated Oct. 6, 2008", 14 pgs.

"U.S. Appl. No. 11/695,545, Restriction Requirement dated Oct. 6, 2008", 10 pgs.

"Chinese Application Serial No. 200580028979.2, First Office Action dated Dec. 12, 2008", 7 pgs.

(56) References Cited

OTHER PUBLICATIONS

"Chinese Application Serial No. 200980117455.9, First Office Action dated Apr. 12, 2012", 9 pgs.
De Juan, Jr., E, "Expandable Nasolacrimal Drainage System Implants", U.S. Appl. No. 60/970,696, filed Sep. 7, 2007, 82 pgs.
De Juan, Jr., E, "Manufacture of Expandable Nasolacrimal Drainage System Implants", U.S. Appl. No. 60/970,720, filed Sep. 7, 2007, 57 pgs.
De Juan, Jr., E, "Multiple Drug Delivery Systems and Combinations of Drugs With Punctal Implants", U.S. Appl. No. 60/970,820, filed Sep. 7, 2007, 67 pgs.
"European Application Serial No. 05768122.3. Office Action dated Mar. 31, 2009", 3 pgs.
"European Application Serial No. 09739174.2, Examination Report dated Mar. 6, 2012", 5 pgs.
"International Application Serial No. PCT/US07/65792, International Search Report dated Nov. 20, 2008", 2 pgs.
"International Application Serial No. PCT/US07/65792, International Written Opinion dated Nov. 20, 2008", 5 pgs.
"International Application Serial No. PCT/US2007/065789, International Search Report dated Aug. 13, 2008", 3 pgs.
"International Application Serial No. PCT/US2007/065789, Written Opinion dated Aug. 13, 2008", 5 pgs.
"International Application Serial No. PCT/US2008/010479, International Search Report dated Dec. 15, 2008", 6 pgs.
"International Application Serial No. PCT/US2008/010479, Written Opinion dated Dec. 15, 2008", 7 pgs.
"International Application Serial No. PCT/US2008/010487, International Search Report dated May 25, 2009", 5 pgs.
"International Application Serial No. PCT/US2008/010487, Written Opinion dated May 25, 2009", 8 pgs.
"International Application Serial No. PCT/US2009/002611, International Preliminary Report on Patentability dated on Nov. 11, 2010", 8 pgs.
"International Application Serial No. PCT/US2009002611, International Search Report and Written Opinion dated Jul. 1, 2010", 14 pgs.
"Israeli Application Serial No. 194514, Notice of Defects dated Sep. 12, 2011".
Lazar, E, "Treatment Medium Delivery Device and Methods for Delivery of Such Treatment Mediums to the Eye Using Such a Delivery Device", U.S. Appl. No. 11/571,147, filed Dec. 21, 2006, 33 pgs.
Reich, Jr., Carl J, "Manufacture of Drug Cores for Sustained Release of Therapeutic Agents", U.S. Appl. No. 60/970,699, filed Sep. 7, 2007, 66 pgs.
Reich, Jr., Carl J, "Nasolacrimal Drainage System Implants for Drug Delivery", U.S. Appl. No. 60/970,709, filed Sep. 7, 2007, 103 pgs.

\* cited by examiner

COMPOSITE LACRIMAL INSERT AND RELATED METHODS

CLAIM OF PRIORITY

This application is a Continuation application of U.S. Ser. No. 12/432,553, filed 29 Apr. 2009, which claims the benefit of priority under 35 U.S.C. §119(e) from U.S. Provisional Ser. No. 61/049,337 filed 30 Apr. 2008, the entire contents of which are incorporated herein by reference.

TECHNICAL FIELD

This patent document pertains generally to ophthalmic devices, and particularly to ocular implants. More particularly, but not by way of limitation, this patent document pertains to lacrimal implants, methods of making such implants, and methods of treating ocular, respiration or other diseases or disorders using such implants.

BACKGROUND

A variety of challenges face patients and physicians in the area of ocular and respiration disease or disorder management, including adequate drug delivery to the eyes or nasal passage and treatment of dry eyes. In ocular management, for example, many current ocular drug delivery systems require repetitive manual drug administration and are often ineffective due to a lack of patient compliance or inadequate drug concentrations reaching the eye. Many current tear flow blockage techniques also have drawbacks, including being irreversible in nature.

In order to eye treat infection, inflammation of the eye, glaucoma and other ocular diseases or disorders, drugs are often required to be administered to the eye. A conventional method of drug delivery is by topical drop application to the eye's surface. Topical eye drops, though effective, can be inefficient. As one example, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Moreover, topically applied drugs often have a peak ocular effect for about two hours post-application, after which additional applications of the drugs should be, but are often not, administered to maintain the desired drug therapeutic benefit.

To compound ocular management difficulty, patients often do not use their eye drops as prescribed. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

Conditions of dry eye have been treated by blocking the tear flow from the eye into and through the lacrimal canaliculus. This has involved closing the canalicular canal by stitching the punctal opening shut or by using electrical or laser cauterization to seal the punctal opening. Although such procedures can provide the desired result of blocking tear flow to treat a dry eye, they are unfortunately not reversible without reconstructive surgery.

In a field different from ocular management, control of respiration-related (e.g., allergies) diseases or disorders often requires repetitive manual digestion or other intake of a medication, and as such, can be ineffective due to a lack of patient compliance or non-localized drug delivery.

Exemplary Aspects, Examples, and Embodiments of the Invention

The present inventors have recognized, among other things, one promising approach of drug delivery to an eye or nasal passage system, for example, can be to place a removable, drug-releasing lacrimal implant into a lacrimal punctum. It is believed that by allowing for the sustained release of one or more drugs, the present lacrimal implants can overcome some of the drawbacks associated with current drug administration (i.e., manual drop instillation or digestion), such as poor patient compliance, waste, untimely application, or non-localized delivery. One promising approach to successful blocking of tear flow from the eye is to place a removable, but retainable, lacrimal implant into the lacrimal punctum. The present inventors have further recognized, among other things, the lacrimal implant can benefit from one or more of the ability to be easily implanted and removed via controlled biasing of the lacrimal punctum or canaliculus, the ability to be securely and comfortably retainable in the lacrimal punctum upon implantation, and, when made and used as a drug delivery system, the ability to allow for the sustained, localized release of one or more drugs at a desired therapeutic level for an extended period of time.

Lacrimal implants for treating diseases or disorders are disclosed. Methods of making such implants, and methods of treating ocular or respiration diseases or disorders using such implants are also disclosed.

In Example 1, a lacrimal implant comprises an implant body, including first and second portions, sized and shaped for at least partial insertion into a lacrimal canaliculus, the first portion including a first biocompatible polymer configured to swell less than 100 wt % when in contact with an aqueous medium, the second portion including a second biocompatible polymer configured to swell greater than 100 wt % when in contact with an aqueous medium; wherein the first and second biocompatible polymers adhere at a junction between the first portion and the second portion.

In Example 2, the lacrimal implant of Example 1 is optionally configured such that the first biocompatible polymer includes a urethane-based material.

In Example 3, the lacrimal implant of at least one of Examples 1 or 2 is optionally configured such that the first biocompatible polymer includes a polyurethane polymer or copolymer.

In Example 4, the lacrimal implant of at least one of Examples 1-3 is optionally configured such that the second biocompatible polymer includes a urethane-based material.

In Example 5, the lacrimal implant of at least one of Examples 1-4 is optionally configured such that the second biocompatible polymer includes a hydrogel-forming polyurethane polymer or copolymer.

In Example 6, the lacrimal implant of at least one of Examples 1-5 is optionally configured such that the second biocompatible polymer includes a hydrogel-forming polyurethane polymer or copolymer, and wherein the polymer or copolymer can swell from about 100 wt % to about 200 wt % when contacted with an aqueous medium.

In Example 7, the lacrimal implant of at least one of Examples 1-6 is optionally configured such that the second biocompatible polymer includes a polyurethane hydrogel adapted to swell 500-2000 wt % upon exposure to an aqueous medium.

In Example 8, the lacrimal implant of at least one of Examples 1-7 is optionally configured such that the first polymer, the second polymer, or both, includes a polyurethane-silicone copolymer, a polyurethane-carbonate copolymer, an aliphatic polyurethane, an aromatic polyurethane, or any combination thereof.

In Example 9, the lacrimal implant of at least one of Examples 1-8 optionally comprises an exterior coating or sheath, the coating or sheath being configured to expand when the second polymer comes into contact with the aqueous medium and swells thereby.

In Example 10, the lacrimal implant of at least one of Examples 1-9 is optionally configured such that the second portion is disposed as a coating on a first part of an external surface of the first portion, and wherein a second part of the external surface of the first portion is disposed adjacent to the proximal end and is uncoated.

In Example 11, the lacrimal implant of at least one of Examples 1-10 is optionally configured such that the junction comprises an intermediate member including a third biocompatible polymer, the third biocompatible polymer configured to adhere to both the first biocompatible polymer and the second biocompatible polymer, and configured to swell upon contact with an aqueous medium to a greater degree than the first polymer but to a lesser degree than the second polymer.

In Example 12, the lacrimal implant of Example 11 is optionally configured such that the third polymer includes a polyurethane polymer or copolymer, a polyurethane-silicone copolymer, a polyurethane-carbonate copolymer, an aliphatic polyurethane, an aromatic polyurethane, or any combination thereof.

In Example 13, the lacrimal implant of Example 12 is optionally configured such that the third polymer is configured to absorb about 50% to about 200% water.

In Example 14, the lacrimal implant of at least one of Examples 11-13 is optionally configured such that the strength of an adhesion between the first biocompatible polymer and the third biocompatible polymer, or between the second biocompatible polymer and the third biocompatible polymer, or both, is stronger than a strength of adhesion between the first and second biocompatible polymers.

In Example 15, the lacrimal implant of at least one of Examples 1-14 is optionally configured such that the first portion comprises a base member extending from a proximal end, configured to sit at or near a lacrimal punctum when implanted and including a first diameter, to a distal end portion, configured for insertion through the lacrimal punctum into the lacrimal canaliculus when implanted and having a second diameter less than the first diameter.

In Example 16, the lacrimal implant of Example 15 is optionally configured such that a shape of the base member is configured to provide sufficient surface area for adhesion of the first biocompatible polymer to the second biocompatible polymer, such that the first portion and the second portion do not separate at the junction when the implant body is withdrawn under tension from the lacrimal canaliculus and the second portion has swelled from contact with the aqueous medium.

In Example 17, the lacrimal implant of Example 16 is optionally configured such that a surface of the first portion is chemically modified or is treated with ionizing radiation or electron beam radiation to bond with the second portion to resist separation under tension.

In Example 18, the lacrimal implant of at least one of Examples 15-17 is optionally configured such that the base member includes one or more arm members protruding from an outer surface thereof.

In Example 19, the lacrimal implant of Examples 18 is optionally configured such that at least one of the one or more arm members protrude laterally relative to a longitudinal axis of the base member.

In Example 20, the lacrimal implant of at least one of Examples 18 or 19 is optionally configured such that the one or more arm members comprise a cross-sectional size greater than an adjacent portion of the base member.

In Example 21, the lacrimal implant of at least one of Examples 15-20 is optionally configured such that the base member includes one or more voids sized to receive a portion of the second portion upon coupling.

In Example 22, the lacrimal implant of at least one of Examples 15-21 is optionally configured such that the second portion comprises an expandable retention member coupled at least partially over the base member, the expandable retention member configured to swell via absorption of an aqueous medium after insertion into the lacrimal canaliculus.

In Example 23, the lacrimal implant of Example 22 is optionally configured such that the expandable retention member substantially envelops the base member.

In Example 24, the lacrimal implant of at least one of Examples 22 or 23 is optionally configured such that the expandable retention member includes a gel configured to at least partially conform to a size and shape of the lacrimal canaliculus.

In Example 25, the lacrimal implant of at least one of Examples 22-24 is optionally configured such that the base member includes a longitudinal axis, and wherein the expandable retention member includes at least one longitudinal swelling axis extending laterally relative to the longitudinal axis of the base member.

In Example 26, the lacrimal implant of at least one of Examples 22-25 is optionally configured such that the expandable retention member is configured to at least partially extend toward a horizontal section of the lacrimal canaliculus.

In Example 27, the lacrimal implant of at least one of Examples 22-26 is optionally configured such that the expandable retention member is configured to at least partially extend toward an ampulla of a lacrimal canaliculus.

In Example 28, the lacrimal implant of at least one of Examples 1-27 optionally comprises a first supply of a first active agent included in the first portion, the first supply configured to provide a release of the first active agent to an eye.

In Example 29, the lacrimal implant of Example 28 is optionally configured such that the first portion includes a cavity extending inward from a proximal end of the first portion, the cavity comprising the first supply to provide the release of the first active agent to the eye.

In Example 30, the lacrimal implant of at least one of Examples 28 or 29 is optionally configured such that the first supply includes a solid matrix comprising a mixture of silicone and the first active agent.

In Example 31, the lacrimal implant of at least one of Examples 28-30 is optionally configured such that the first supply is dispersed within the first polymer.

In Example 32, the lacrimal implant of at least one of Examples 28-31 is optionally configured such that the first supply includes at least one exposed surface near a proximal end of the first portion to provide release of the first active agent to the eye.

In Example 33, the lacrimal implant of Example 32 is optionally configured such that the at least one exposed surface is positioned above the proximal end of the first portion such that the first supply at least partially protrudes outside of the implant body.

In Example 34, the lacrimal implant of at least one of Examples 28-33 optionally comprises a second supply of a second active agent included in the second portion, the second supply configured to provide a release of the second active agent to one or both of a lacrimal canaliculus wall or a nasolacrimal system after contact with an aqueous medium.

In Example 35, the lacrimal implant of at least one of Examples 28-34 is optionally configured such that the first or second active agent comprises an anti-glaucoma medicament, an antimicrobial agent, a corticosteroid or other anti-inflammatory, a decongestant, an agent that prevents of modifies an allergic response, a mast cell stabilizer, a cycloplegic, a mydriatic, or a combination thereof.

In Example 36, the lacrimal implant of Example 35 is optionally configured such that the anti-glaucoma medicament comprises an adrenergic agonist, an adrenergic antagonists, a systemic or topical carbonic anhydrase inhibitor, a prostaglandin or hypotensive lipid, or a combination thereof.

In Example 37, the lacrimal implant of Example 36 is optionally configured such that the prostaglandin comprises bimatoprost, travoprost, or latanoprost, or a combination thereof.

In Example 38, the lacrimal implant of Example 35 is optionally configured such that the antimicrobial agent comprises an antibiotic, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, an antifungal, amphotericin B, miconazole, an antiviral, idoxuridine trifluorothymidine, acyclovir, gancyclovir, or interferon, or a combination thereof.

In Example 39, the lacrimal implant of Example 36 is optionally configured such that the corticosteroid or other anti-inflammatory comprises cyclosporine, hydrocortisone, hydrocortisone acetate, dexamethasone, dexamethasone 21-phosphate, fluocinolone, medrysone, methylprednisolone, prednisolone, prednisolone 21-phosphate, prednisolone acetate, fluoromethalone, betamethasone, triamcinolone, triamcinolone acetonide, cortisone, flumetholone, a non steroidal anti-inflammatory, salicylate, indomethacin, ibuprofen, diclofenac, flurbiprofen, piroxicam indomethacin, ibuprofen, naxopren, piroxicam, nabumetone, ketorolac, bromfenac, nepafenac or suprofen, or combinations thereof.

In Example 40, the lacrimal implant of Example 36 is optionally configured such that the decongestant comprises a vasoconstrictor, phenylephrine, naphazoline, or tetrahydrazoline, or a combination thereof.

In Example 41, the lacrimal implant of Example 36 is optionally configured such that the agent that prevents or modifies an allergic response comprises an antihistamine, a cytokine inhibitor, a leucotriene inhibitor, an IgE inhibitor, an immunomodulator, cyclosporine, or a combination thereof.

In Example 42, the lacrimal implant of at least one of Examples 1-41 is optionally configured such that an intermediate section of the first portion includes a coupling void and a coupling arm sized and shaped to lock within the coupling void.

In Example 43, the lacrimal implant of at least one of Examples 1-42 is optionally configured such that the implant body is non-biodegradable when implanted within a human subject.

In Example 44, the lacrimal implant of at least one of Examples 1-42 optionally comprises a lateral projection affixed to a proximal end of the first portion, the lateral projection having a size and shape configured to rest on an exterior of the lacrimal punctum when a distal end of the first portion is positioned within a lacrimal canaliculus.

In Example 45, the lacrimal implant of at least one of Examples 1-44 is optionally configured such that the implant body in physical shape comprises a substantially cylindrical or conical region.

In Example 46, a kit comprises the lacrimal implant of at least one of Examples 1-45, and an instruction for using the lacrimal implant to treat an eye disease.

In Example 47, a method of making the lacrimal implant of at least one of Examples 1-45 comprises use of a melt of the polyurethane polymer or copolymer.

In Example 48, a method of making the lacrimal implant of at least one of Examples 1-45 comprises injection molding the first portion, the second portion, or both, using respectively a melt of the first polymer, the second polymer, or melts of both polymers.

In Example 49, a method of making the lacrimal implant of at least one of Examples 1-45 comprises injection molding the first portion, the second portion, or both, using respectively a melt of the first polymer, the second polymer, or melts of both polymers, wherein an intermediate member is disposed as a melt between the first portion and the second portion.

In Example 50, a lacrimal implant comprises a unitary implant body sized to at least partially pass through a lacrimal punctum and be at least partially positioned within a lacrimal canaliculus, the implant body extending from a proximal end portion to a distal end portion, the proximal end portion including a cavity, the distal end portion including a base member having a diameter less than a diameter of the proximal end portion; a drug supply included in the cavity, the drug supply configured to provide a release of a first active agent to an eye; and an expandable retention member coupled at least partially over the base member, the expandable retention member including a dehydrated material hydratable an aqueous medium to swell from a first diameter to a second diameter greater than the first diameter.

In Example 51, the lacrimal implant of Example 50 is optionally configured such that the expandable retention member fully envelopes the base member.

In Example 52, the lacrimal implant of at least one of Examples 50 or 51 is optionally configured such that the implant body includes a urethane-based material.

In Example 53, the lacrimal implant of at least one of Examples 50-52 optionally comprises a second active agent included in the expandable retention member, the expandable retention member configured to provide a release of the second active agent after contact with the aqueous medium.

In Example 54, the lacrimal implant of at least one of Examples 50-53 is optionally configured such that the base member includes one or more arm members laterally protruding from an outer surface thereof.

In Example 55, the lacrimal implant of at least one of Examples 50-54 is optionally configured such that the expandable retention member includes a urethane-based hydrogel material.

In Example 56, the lacrimal implant of at least one of Examples 50-55 is optionally configured such that the second diameter of the expandable retention member is configured to be at least about 5 times greater than the first diameter of the expandable retention member.

In Example 57, the lacrimal implant of at least one of Examples 50-56 is optionally configured such that the length of the base member is at least about one-third the total length of the implant body.

In Example 58, the lacrimal implant of at least one of Examples 50-57 is optionally configured such that the length of the base member is at least about one-half the total length of the implant body.

In Example 59, a kit comprises the lacrimal implant of any of claims 50-58, and an instruction for using the lacrimal implant to treat an eye disease.

In Example 60, a method comprises forming an implant body, including first and second portions, sized for at least partial insertion into a lacrimal canaliculus, including forming the first portion from a first biocompatible polymer configured to swell less than 100 wt % when in contact with an aqueous medium, and forming the second portion from a second biocompatible polymer configured to swell greater than 100 wt % when in contact with an aqueous medium; and coupling the first and second biocompatible polymers at a junction between the first portion and the second portion.

In Example 61, the method of Example 60 optionally comprises disposing an intermediate member including a third biocompatible polymer between the first and second portions, the third biocompatible polymer configured to adhere to the first biocompatible polymer on a first surface and adhere to the second biocompatible polymer on a second surface.

In Example 62, the method of at least one of Examples 60 or 61 is optionally configured such that forming the first portion includes forming a base member extending from a proximal end, configured to sit at or near a lacrimal punctum when implanted, to a distal end portion, configured for insertion through the lacrimal punctum into the lacrimal canaliculus when implanted, including forming one or more arm members protruding from an outer surface of the base member.

In Example 63, the method of Example 62 is optionally configured such that adhering the first and second biocompatible polymers includes coupling an expandable retention member at least partially over the base member such that an outer surface of the expandable retention member can absorb the aqueous medium after insertion into the lacrimal canaliculus.

In Example 64, the method of Example 63 is optionally configured such that coupling the expandable retention member at least partially over the base member includes fully surrounding the base member with the expandable retention member.

In Example 65, the method of at least one of Examples 60-64 optionally comprises providing a first supply of a first active agent in the first portion, the first supply configured to provide a release of the first active agent to an eye.

In Example 66, the method of at least one of Examples 60-65 is optionally configured such that forming the first and second portions from a polymer includes forming a unitary implant body from a urethane-based material.

In Example 67, the method of at least one of Examples 63-66 optionally comprises disposing an intermediate member between an outer surface of the base member and an inner surface of the expandable retention member, the intermediate member configured to absorb a greater amount of fluid than the polymer of the second portion but less fluid than a swellable polymer of the expandable retention member.

In Example 68, the method of at least one of Examples 60-67 is optionally configured such that forming the implant body includes forming a cavity extending inward from a proximal end of the first portion, including configuring the cavity to include a drug supply and positioning at least one exposed surface of the drug supply near the proximal end.

In Example 69, the method of Example 68 is optionally configured such that positioning the at least one exposed surface of the drug supply near the proximal end includes positioning the at least one exposed surface above the proximal end such that the first supply at least partially protrudes outside of the implant body.

In Example 70, the method of at least one of Examples 63-69 is optionally configured such that forming the second portion including the base member includes forming one or more arm members protruding laterally from an outer surface of the base member, to thereby increase the surface area for coupling of the expandable retention member.

In Example 71, the method of at least one of Examples 63-70 is optionally configured such that coupling the expandable retention member includes molding a urethane-based hydrogel over the base member.

In Example 72, the method of at least one of Examples 63-72 is optionally configured such that coupling the expandable retention member includes dip coating the base member with a urethane-based hydrogel.

In Example 73, the method of at least one of Example 63-72 is optionally configured such that coupling the expandable retention member includes disposing a hydrogel sleeve over an outer surface of the base member.

In Example 74, a method of treating a subject having an eye disorder comprises inserting a lacrimal implant into at least one lacrimal canaliculus, the lacrimal implant comprising, an implant body, including first and second portions, sized and shaped for at least partial insertion into a lacrimal canaliculus, the first portion including a first biocompatible polymer configured to swell less than 100 wt % when in contact with an aqueous medium, the second portion including a second biocompatible polymer configured to swell greater than 100 wt % when in contact with an aqueous medium; wherein the first and second biocompatible polymers adhere at a junction between the first portion and the second portion.

In Example 75, the method of Example 74 is optionally configured such that inserting the lacrimal implant includes partially inserting the implant body through a lacrimal punctum until a removal projection extending laterally from the proximal end of the first portion is positioned outside and adjacent to the lacrimal punctum.

In Example 76, the method of at least one of Examples 74 or 75 is optionally configured such that inserting the lacrimal implant includes positioning a supply of an active agent, included in the first portion, adjacent an eye of the subject.

In Example 77, the method of Example 76 is optionally configured such that the active agent is configured to treat at least one of a glaucoma disease or a seasonal allergy.

In Example 78, the method of at least one of Examples 76 or 77 is optionally configured such that a period of time over which the active agent is released includes at least one week, at least one month, or at least three months.

In Example 79, the method of at least one of Examples 74-78 optionally comprises removing the inserted implant body from the lacrimal punctum.

In Example 80, the method of Example 79 optionally comprises replacing the lacrimal implant that has been removed with a second lacrimal implant including a supply of an active agent following an interval of time.

In Example 81, the method of Example 80 is optionally configured such that replacing the lacrimal implant is repeated until the subject no longer requires treatment.

In Example 82, a method of administering a medicament to the eye, or to surrounding tissue, or both, of a patient having a malcondition for treatment of which administration of the medicament is medically indicated comprises inserting the lacrimal implant of any of claims 1 through 45, or a lacrimal implant made by the method of any of claims 47 through 49, wherein the implant comprises the medicament dispersed therein, into a punctal canal of a patient in need thereof, such that the implant is placed in contact with an aqueous medium and the implant undergoes swelling to secure the implant within the punctal canal, and such that the medicament is released into the eye or surrounding tissues, or both, from the implant over a period of time.

In Example 83, a method of administering a medicament to the eye, or to surrounding tissue, or both, of a patient having a malcondition for treatment of which administration of the medicament is medically indicated comprises inserting the lacrimal implant of any of claims 1 through 45, or a lacrimal implant made by the method of any of claims 47 through 49, wherein the implant comprises a drug-releasing insert with the medicament dispersed therein, into a punctal canal of a patient in need thereof, such that the implant is placed in contact with an aqueous medium and the implant undergoes swelling to secure the implant within the punctal canal, and such that the medicament is released into the eye or surrounding tissues, or both, from the drug-releasing insert over a period of time.

In Example 84, a method of administering a medicament to the eye, or to surrounding tissue, or both, of a patient having a malcondition for treatment of which administration of the medicament is medically indicated comprises inserting the lacrimal implant of any of claims 1 through 45, or a lacrimal implant made by the method of any of claims 47 through 49, wherein the first portion comprises an active substance dispersed therein, into a punctal canal of a patient in need thereof, such that the second polymer is placed in contact with an aqueous medium and the second polymer undergoes swelling to secure the implant within the punctal canal, and such that the active agent is released into the eye or surrounding tissues, or both, from the first polymer over a period of time.

In Example 85, a method of administering a medicament to the eye, or to surrounding tissue, or both, of a patient having a malcondition for treatment of which administration of the medicament is medically indicated comprises inserting the lacrimal implant of any of claims 1 through 45, or a lacrimal implant made by the method of any of claims 47 through 49, wherein the first portion comprises a drug-releasing insert with an active substance dispersed therein, into a punctal canal of a patient in need thereof, such that the second polymer is placed in contact with an aqueous medium and the second polymer undergoes swelling to secure the implant within the punctal canal, and such that the active agent is released into the eye or surrounding tissues, or both, from the drug-releasing insert over a period of time.

In Example 86, the method of at least one of Examples 82-85 is optionally configured such that the period of time is about 1 week to about 6 months.

In Example 87, the method of at least one of Examples 82-86 is optionally configured such that the medicament comprises an anti-glaucoma medicament, an antimicrobial agent, a corticosteroid or other anti-inflammatory, a decongestant, an agent that prevents of modifies an allergic response, a mast cell stabilizer, a cycloplegic, a mydriatic, or a combination thereof.

In Example 88, the method of Example 87 is optionally configured such that the anti-glaucoma medicament comprises an adrenergic agonist, an adrenergic antagonists, a systemic or topical carbonic anhydrase inhibitor, a prostaglandin or hypotensive lipid, or a combination thereof.

In Example 89, the method of Example 88 is optionally configured such that the prostaglandin comprises bimatoprost, travoprost, or latanoprost, or a combination thereof.

In Example 90, the method of at least one of Examples 82-89 is optionally configured such that the medicament is indicated for treating high eye pressure/intraocular pressure in people with open-angle glaucoma or ocular hypertension.

In Example 91, the method of Example 87 is optionally configured such that the antimicrobial agent comprises an antibiotic, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, an antifungal, amphotericin B, miconazole, an antiviral, idoxuridine trifluorothymidine, acyclovir, gancyclovir, or interferon, or a combination thereof.

In Example 92, the method of Example 87 is optionally configured such that the corticosteroid or other anti-inflammatory comprises cyclosporine, hydrocortisone, hydrocortisone acetate, dexamethasone, dexamethasone 21-phosphate, fluocinolone, medrysone, methylprednisolone, prednisolone, prednisolone 21-phosphate, prednisolone acetate, fluoromethalone, betamethasone, triamcinolone, triamcinolone acetonide, cortisone, flumetholone, a non steroidal anti-inflammatory, salicylate, indomethacin, ibuprofen, diclofenac, flurbiprofen, piroxicam indomethacin, ibuprofen, naxopren, piroxicam, nabumetone, ketorolac, bromfenac, nepafenac, or suprofen or combinations thereof.

In Example 93, the method of Example 87 is optionally configured such that the decongestant comprises a vasoconstrictor, phenylephrine, naphazoline, or tetrahydrazoline, or a combination thereof.

In Example 94, the method of Example 87 is optionally configured such that the agent that prevents of modifies an allergic response comprises an antihistamine, a cytokine inhibitor, a leucotriene inhibitor, an IgE inhibitor, an immunomodulator, cyclosporine, or a combination thereof.

These and other examples, advantages, and features of the present lacrimal implants and methods will be set forth in part in following Detailed Description. This Summary is intended to provide an overview of the subject matter of the present patent document. It is not intended to provide an exclusive or exhaustive explanation of the present subject matter. The Detailed Description is included to provide further information about the present patent document.

BRIEF DESCRIPTION OF THE DRAWINGS

In the drawings, like numerals have been used to describe similar components throughout the several views. Like numerals having different letter suffixes have been used to represent different instances of similar components. The drawings illustrate generally, by way of example, but not by way of limitation, various embodiments discussed in the present document.

DETAILED DESCRIPTION

In this patent document, biocompatible lacrimal implants and related methods providing secure, biasing retention within a lacrimal punctum of an eye are described. The lacrimal implants can comprise an implant body configured for at least partial insertion through the lacrimal punctum and into an associated lacrimal canaliculus. The implant body can include first and second portions, in which the first portion is formed from a polymer and includes a first diameter and the second portion is also formed from a polymer and includes a base member having a second diameter. In various examples, the second diameter of the base member is less than the first diameter of the first body portion. An expandable retention member is coupled at least partially over the base member and is configured to swell via absorption of lacrimal fluid after insertion into the lacrimal punctum. In this way, at least a portion of the expandable retention member can be biased against at least a portion of a lacrimal canaliculus wall to retain an implant position of the lacrimal implant. In an example, the lacrimal implant includes a punctual plug. In various examples, the lacrimal implant can further comprise a drug or other agent supply included in at least one of the first portion or the expandable retention member, such as to provide a sustained release of a therapeutic agent to one or both of an eye or a nasal passage, for instance.

The present lacrimal implants can be securely retained in or near an eye, such as for one or more of successfully blocking the flow of tears from the eye, or providing sustained delivery of a drug or other therapeutic agent to the eye, nasal passage or other portion of the nasolacrimal system. Configuring the lacrimal implant to include an expandable retention member coupled at least partially over a second, smaller diameter portion of the implant body can inhibit the lacrimal implant from inadvertently coming out of an implanted lacrimal punctum and canalicular position, and can be used to at least partially block movement of a fluid through the lacrimal canaliculus. In addition, by configuring the expandable retention member to be coupled at least partially over the second, smaller diameter portion of the implant body, adequate adhesion between the expandable retention member (or optionally, an intermediate swellable member) and the implant body is possible via a relatively large surface coupling area.

Figure 1:
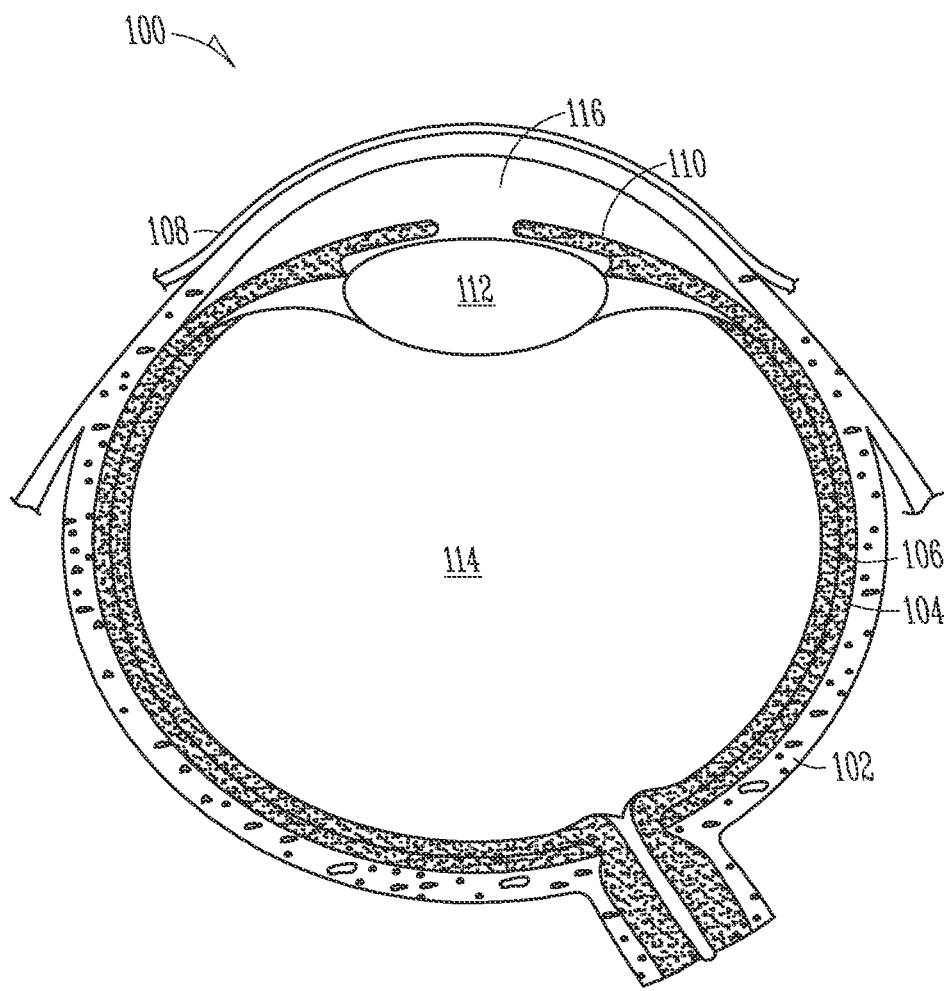
FIGS. 1-2 illustrate examples of schematic views of anatomical tissue structures associated with the eye, such tissue structures providing a suitable environment in which the present lacrimal implants can be used.
Figure 2:
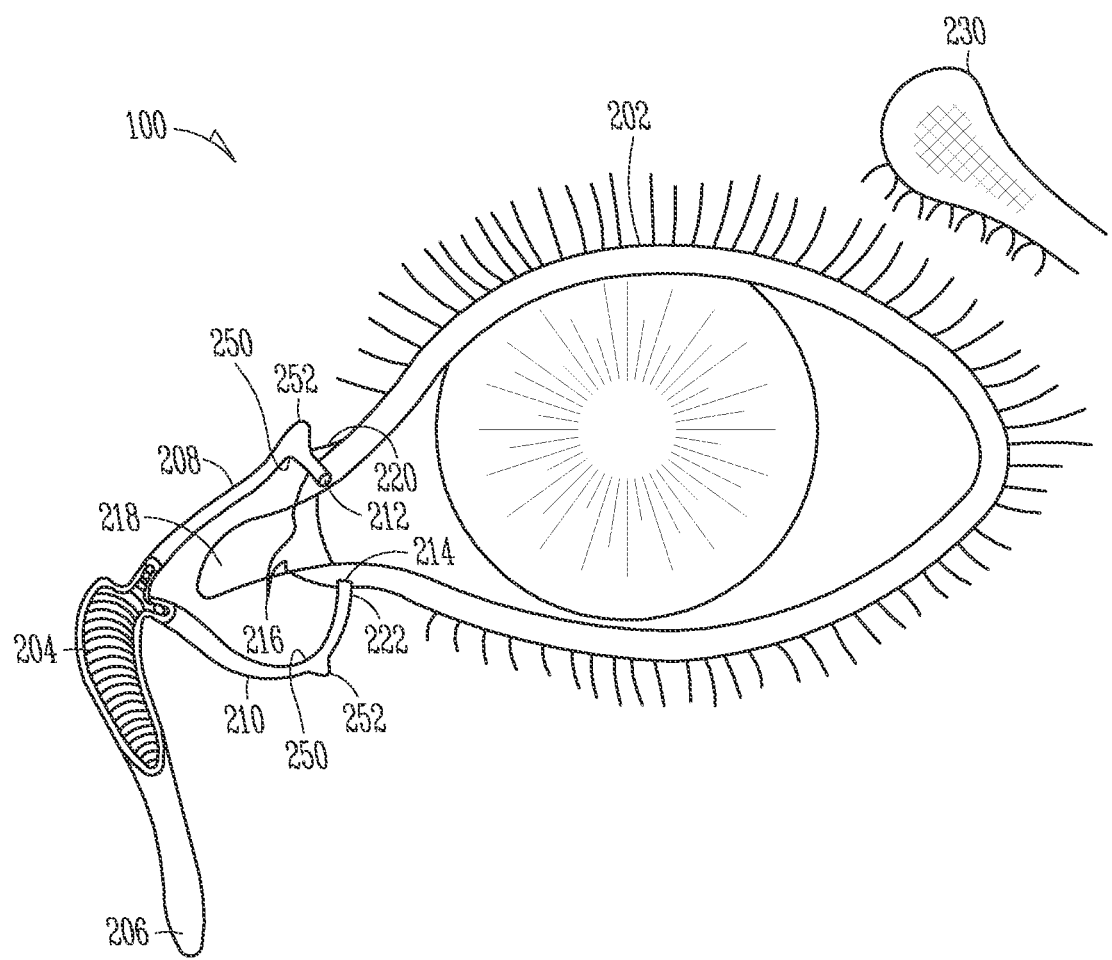

FIGS. 1-2 illustrate examples of schematic views of anatomical tissue structures associated with an eye 100. The anatomical tissue structures shown are suitable for treatment using the lacrimal implants and methods discussed herein. The eye 100 is a spherical structure including a wall having three layers: the outer sclera 102, the middle choroid layer 104 and the inner retina 106. The sclera 102 includes a tough fibrous coating that protects the inner layers. It is mostly white except for the transparent area at the front, the cornea 108, which allows light to enter the eye 100.

The choroid layer 104, situated inside the sclera 102, contains many blood vessels and is modified at the front of the eye 100 as the pigmented iris 110. The biconvex lens 112 is situated just behind the pupil. The chamber 114 behind the lens 112 is filled with vitreous humour, a gelatinous substance. The anterior and posterior chambers 116 are situated between the cornea 108 and iris 110, respectively and filled with aqueous humour. At the back of the eye 100 is the light-detecting retina 106.

The cornea 108 is an optically transparent tissue that conveys images to the back of the eye 100. It includes avascular tissue to which nutrients and oxygen are supplied via bathing with lacrimal fluid and aqueous humour as well as from blood vessels that line the junction between the cornea 108 and sclera 102. The cornea 108 includes one pathway for the permeation of drugs into the eye 100.

Other anatomical tissue structures associated with the eye 100 include the lacrimal drainage system, which includes a secretory system 230, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids 202 and the tear meniscus around the lid edges of an open eye, which spread tears over the ocular surface by blinking, thus reducing dry areas from developing.

The excretory part of the lacrimal drainage system includes, in flow order of drainage, the lacrimal puncta, the lacrimal canaliculi, the lacrimal sac 204 and the lacrimal duct 206. From the lacrimal duct 206, tears and other flowable materials drain into a passage of the nasal system. The lacrimal canaliculi include an upper (superior) lacrimal canaliculus 208 and a lower (inferior) lacrimal canaliculus 210, which respectively terminate near the eye 100 in an upper 212 and lower 214 lacrimal punctum. The upper 212 and lower 214 punctum are slightly elevated at the medial end of a lid margin at the junction 216 of the ciliary and lacrimal portions near a conjunctival sac 218. The upper 212 and lower 214 punctum are generally round or slightly ovoid openings surrounded by a connective ring of tissue. Each of the puncta 212, 214 leads into a vertical portion 220, 222 of their respective canaliculus before turning more horizontal at a canaliculus curvature 250 to join one another at the entrance of the lacrimal sac 204. The canaliculi 208, 210 are generally tubular in shape and lined by stratified squamous epithelium surrounded by elastic tissue, which permits them to be dilated or biased. As shown, a lacrimal canaliculus ampulla 252 exists near an outer edge of the canaliculus curvature 250. In accordance with features of the present subject matter, a lacrimal implant can be inserted through either punctum and into its associated canaliculus.

Figure 3:
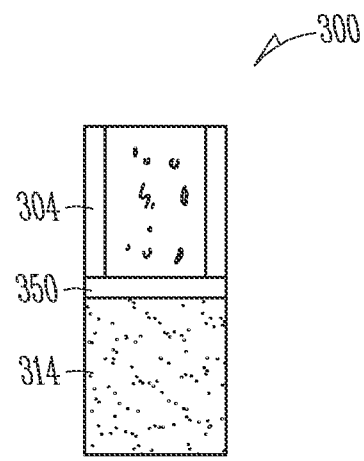
FIG. 3 illustrates an example of a present lacrimal implant showing a "half and half" implant design.

FIG. 3 illustrates an example of a lacrimal implant 300 that can be insertable into a lacrimal punctum 212, 214 (FIG. 2). The insertion of the lacrimal implant 300 into a lacrimal punctum 212, 214 can allow for one or more of inhibition or blockage of tear flow through a lacrimal canaliculus 208, 210 (FIG. 2) (e.g., to treat dry eyes), or the sustained delivery of a therapeutic agent to an eye (e.g., to treat an infection, inflammation, glaucoma or other ocular diseases or disorders) or nasal passage (e.g., to treat a sinus or allergy disorder). In some examples, a period of time over which the agent is delivered includes at least one week, at least one month, or at least three months. In some examples, the lacrimal implant 300 includes a width between about 0.3 millimeters to about 1.5 millimeters. In some examples, the lacrimal implant 300 includes a length between about 1.5 millimeters to about 6 millimeters, such as between about 2 millimeters to about 3 millimeters.

In an example, the lacrimal implant 300 comprises a polyurethane polymer or copolymer. Typically, lacrimal implants are formed of silicone polymers, which can be quite hydrophobic and furthermore are usually prepared by polymerization of a silicone precursor in the presence of a catalyst. However, polyurethane polymers and copolymers can be thermoplastic, and can therefore be melted and cast into a desired form. A medicament can be dispersed within the polyurethane melt, either in molten form itself or as a dispersion of a solid material. Polyurethane polymers and copolymers can also be dissolved in various organic solvents, such as dichloromethane or tetrahydrofuran, then cast into a desired form with removal of the solvent, such as by evaporation. Again, a medicament can be dispersed or dissolved in the organic solvent along with the polyurethane, such that upon removal of the solvent, the polyurethane containing the medicament in a desired form is obtained.

In FIG. 3, the lacrimal implant 300 is shown as a "half and half" implant design. In this example, an expandable retention member 314, such as a swellable material that can be bonded or otherwise coupled over a portion of the lacrimal implant 300 such that it envelops, at least in part, a portion of the lacrimal implant 300, forms a junction with a first portion 304 of the body of the lacrimal implant 300. The first portion 304 of the body of the lacrimal implant 300 can be formed of a first polymer that is biocompatible and swells less than 100 wt % when in contact with an aqueous medium, such as a biocompatible polyurethane polymer or copolymer. For example, the first polymer can comprise a polyurethane-silicone copolymer. An example is Pursil®, a biocompatible, non-biodegradable copolymer adapted for medical use. Other similar materials can also be used, provided they are both biocompatible and substantially non-swelling or minimally swelling when put in contact with an aqueous medium. For example, hydrophilic polyurethanes that do not substantially swell upon contact with an aqueous medium can be used to improve surface wettability of the non-hydrogel component of the lacrimal implant 300. The expandable retention member 314 can be formed of a second polymer that is biocompatible and swells greater than 100 wt % to form a hydrogel when in contact with an aqueous medium, such as a biocompatible hydrogel-forming polyurethane polymer or copolymer. For example, hydrogel-forming materials TG-500 or TG-2000, adapted to swell by as much as 500-2000 wt % upon exposure to an aqueous medium, can be used.

In the half and half design, the expandable retention member 314 is uncovered. The junction between the first portion 304 of the implant body and the expandable retention member 314 includes an intermediate member 350, optionally comprising the third polymer which can have an intermediate degree of swelling in an aqueous medium, and is sufficiently strong to hold the implant intact under a degree of tension, such as when the implant is removed from the punctal canal. The third polymer can be a biocompatible polyurethane polymer or copolymer adapted to adhere to both the first and second polymers. It can be a moderately swelling polymer upon exposure to the aqueous medium.

Figure 4A:
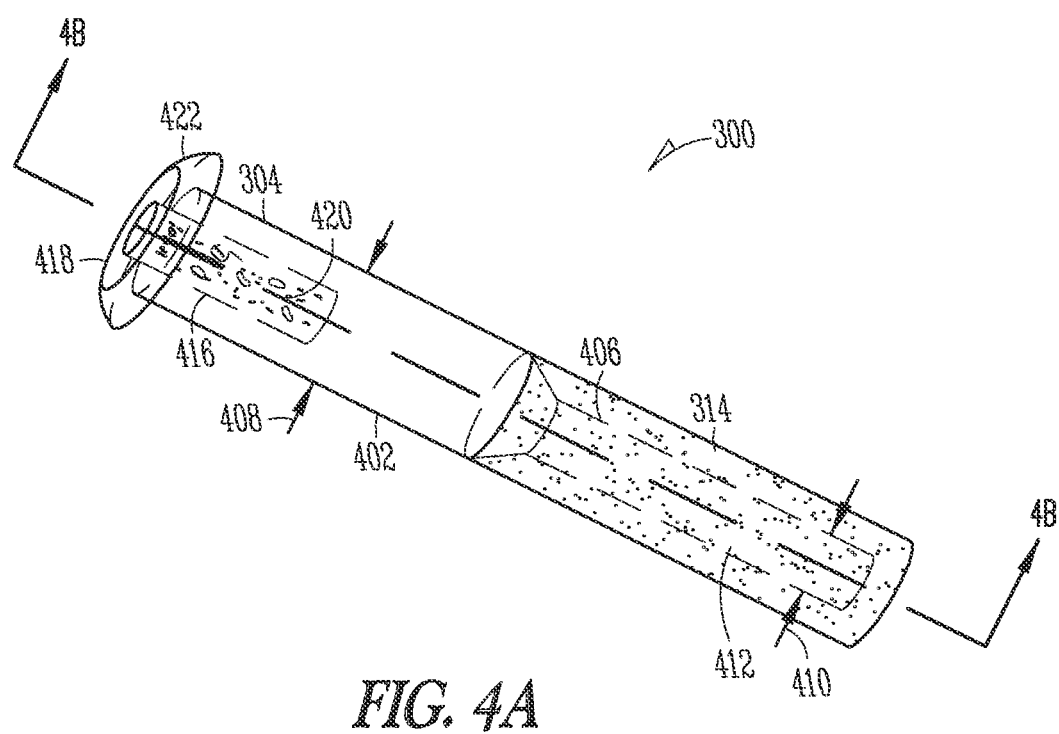
FIG. 4A illustrates an example of an isometric view of a present lacrimal implant, which is configured to be retained within a lacrimal punctum and canalicular anatomy.

FIG. 4A illustrates first portion 304 of the body of the lacrimal implant another example of the lacrimal implant 300 that can be insertable into a lacrimal punctum 212, 214 (FIG. 2). In various examples, the lacrimal implant 300 comprises an implant body 402, including first 304 and second 406 portions, which is sized and shaped for at least partial insertion into a lacrimal punctum 212, 214. The first portion 304 is formed from a polymer and includes a first diameter 408. The second portion 406 is also formed from a polymer and includes a base member 412 (e.g., mandrel or spine-like member) having a second diameter 410, which is less than the first diameter 408. In an example, the first 304 and second 406 portions are integrally coupled and comprise a unitary implant body 402. In an example, as shown in FIGS. 7E-7G, the first 304 and second 406 portions are separate elements, which can be coupled to one another via an engagement between a coupling void and a coupling arm, for instance.

An expandable retention member 314, such as a swellable material, can be bonded or otherwise coupled over the base member 412 such that it envelops, at least in part, a portion of the base member 412. In an example, the expandable retention member substantially envelops the base member 412. As the expandable retention member 314 absorbs or otherwise retains lacrimal or other fluid, such as upon insertion into a lacrimal punctum 212, 214, its size increases and its shape may change thereby urging itself against and slightly biasing a wall of the associated canaliculus 208, 210. It is believed that the expandable retention member 314 will provide retention comfort to a subject and may improve lacrimal implant 300 retention via controlled biasing of the canaliculus 208, 210 wall.

The positioning of the expandable retention member 314 over a portion of the implant body 402 allows the retention member 314 to be freely exposed to lacrimal fluid in situ, thereby allowing for a wide range of potential expansion rates. Further, the base member 412 provides an adequate coupling surface area to which the expandable retention member 314, for example, can adhere such that the material of the expandable retention member 314 does not remain in a lacrimal punctum 212, 214 after the lacrimal implant 300 is removed from the subject. As shown in this example, the expandable retention member 314 can include a non-expanded, "dry or dehydrated" state, which aids insertion through a lacrimal punctum 212, 214 and into the associated lacrimal canaliculus 208, 210. Once placed into a lacrimal canaliculus 208, 210, the expandable retention member 314 can absorb or other retain lacrimal fluid to form an expanded structure.

Figure 4B:
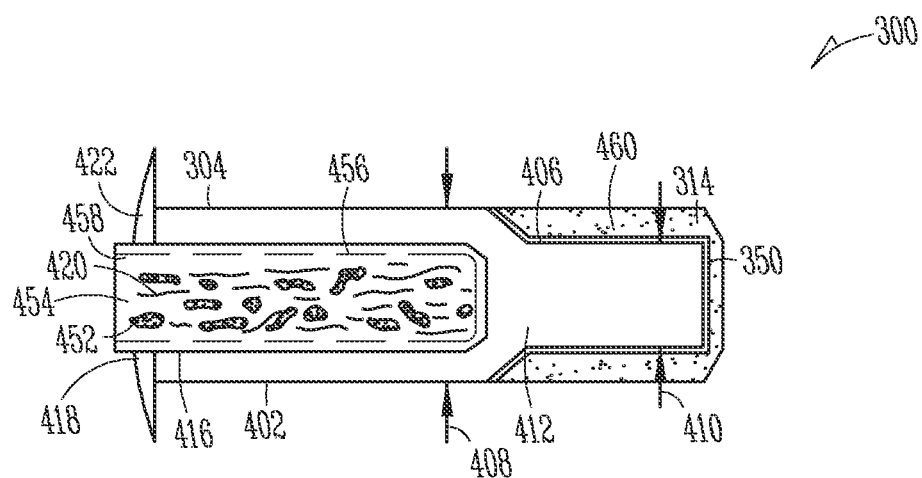
FIG. 4B illustrates an example of a cross-sectional view of a present lacrimal implant taken along a line parallel to a longitudinal axis of the implant, such as along line 3B-3B of FIG. 3A.

In some examples, the implant body 402 can include a cylindrical-like structure comprising a cavity 416 disposed near a proximal end 418 of the first portion 304. In this example, the cavity 416 extends inward from the proximal end 418 and includes a first drug-releasing or other agent-releasing drug supply 420 to provide a sustained drug or other agent release to an eye 100. The drug or other agent release can occur, at least in part, via an exposed surface of the drug supply 420. In an example, such as is shown in FIG. 4B, the exposed surface of the drug supply 420 can be positioned above the proximal end 418 such that the drug supply 420 at least partially protrudes outside of the implant body 402. In some examples, the exposed surface of the drug supply 420 can be flush or slightly below the proximal end 418 such that the drug supply 420 does not protrude outside of the implant body 402.

In some examples, by controlling geometry or a drug concentration gradient near the exposed surface, a predetermined drug or agent release rate can be achieved. For instance, the exposed surface can be constructed with a specific geometry or other technique appropriate to control the release rate of the drug or other agent onto an eye 100, such as on an acute basis, or on a chronic basis between outpatient doctor visits, for example. Further discussion regarding effective release rates of one or more drugs or other agents from a drug supply 420 can be found in commonly-owned DeJuan et al., U.S. patent application Ser. No. 11/695,545, entitled "NASOLACRIMAL DRAINAGE SYSTEM IMPLANTS FOR DRUG THERAPY," which is herein incorporated by reference in its entirety, including its description of obtaining particular release rate ranges.

The implant body 402 can include an integral feedback or other projection 422, such as projections extending laterally at least partially from or around the proximal end 418 of the first implant body portion 304. In an example, the projection 422 includes a partially trimmed head portion extending 360 degrees around the proximal end 418 from an outer implant body surface. In an example, the projection 422 includes a full head portion extending 360 degrees around the proximal end 418 from an outer implant body surface. In an example, the projection 422 includes a cross-sectional shape similar to a flat disk (i.e., relatively flat top and bottom surfaces). In various examples, the projection 422 can be configured to seat against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position. In an example, the projection 422 includes a portion having a diameter of about 0.5-2.0 mm to prevent the lacrimal implant 300 from passing down into the canaliculus 208, 210.

FIG. 4B illustrates an example of a cross-sectional view of a lacrimal implant 300 taken along a line parallel to a longitudinal axis of the implant, such as along line 4B-4B of FIG. 4A. As shown in FIG. 4B, the lacrimal implant 300 comprises an implant body 402, including first 304 and second 406 portions, which is sized and shaped for at least partial insertion into a lacrimal punctum 212, 214 (FIG. 2). The first portion 304 is formed from a polymer and includes a first diameter 408. The second portion 406 is also formed from a polymer and includes a base member 412 (e.g., mandrel or spine) having a second diameter 410, which is less than the first diameter 408. In an example, the base member 412 is at least about one-third the total length of the implant body 402. In an example, the base member 412 is at least about one-half the total length of the implant body 402. In the example shown, the implant body 402 also includes an integral feedback or other projection 422, such as a projection extending laterally at least partially from or around a proximal end 418 of the first implant body portion 304.

In various examples, the implant body 402 can be molded or otherwise formed using an elastic material, such as silicone, polyurethane or other urethane-based material, or combinations thereof. In an example, one or both of the first 304 and second 406 portions include a urethane-based material. In an example, one or both of the first 304 and second 406 portions include a silicone-based material, such as 4840® or PurSil®. In an example, one or both of the first 304 and second 406 portions include a copolymer material, such as polyurethane/silicone, urethane/carbonate, silicone/polyethylene glycol (PEG) or silicone/2hydroxyethyl methacrylate (HEMA). In various examples, the implant body 402 is configured to be non-absorbable in situ and is sufficiently strong to address issues of cutting strength (e.g., during insertion and removal of the lacrimal implant 300) and dimensional stability.

An expandable retention member 314, such as a swellable material, can be bonded or otherwise coupled over the base member 412 such that it envelops, at least in part, a portion of the base member 412. As the expandable retention member absorbs or otherwise retains lacrimal fluid, such as upon insertion into a lacrimal punctum 212, 214, its size increases and its shape may change thereby urging itself against and slightly biasing a wall of the associated canaliculus 208, 210. In various examples, the expandable retention member 314 can be molded or otherwise formed using a swellable material. In an example, the expandable retention member 314 includes a polyurethane hydrogel, such as TG-2000®, TG-500®, or other urethane-based hydrogel. In an example, the expandable retention member 314 includes a thermoset polymer, which may be configured to swell anisotropically. In an example, the expandable retention member 314 includes a gel, which does not maintain its shape upon expansion, but rather conforms to fit the shape of a canaliculus lumen wall or other surrounding structure.

In some examples, the lacrimal implant 300 includes a base member 412 including polyurethane or other urethane-based material and an expandable retention member 314 including a biocompatible polyurethane or other urethane-based swellable material. In an example, a polyurethane hydrogel is coupled directly to an outer surface, such as a plasma-treated outer surface, of the base member 412. As further discussed in commonly-owned Utkhede et al., U.S. patent application Ser. No. 12/231,986, entitled "DRUG CORES FOR SUSTAINED RELEASE OF THERAPEUTIC AGENTS," which is herein incorporated by reference in its entirety and which claims priority in part to U.S. Patent Application No. 61/049,317, urethane-based polymer and copolymer materials allow for a variety of processing methods and bond well to one another.

In some examples, the lacrimal implant 300 includes an intermediate member 350 positioned between a portion of the implant body 402, such as the base member 412, and a portion of the expandable retention member 314. The intermediate member 350 can include a material configured to absorb, when implanted, a greater amount of lacrimal fluid than the polymer of the base member 412 but less lacrimal fluid than the swellable polymer of the expandable retention member 314. The intermediate member 350 can provide the lacrimal implant 300 with integrity, such as between a substantially non-swelling polymer of the implant body 402 and a swelling polymer of the expandable retention member 314. For instance, when the polymer of the expandable retention member 314 swells upon exposure to moisture, it is possible that the expanding polymer will, in the absence of the intermediate member 350, swell away from the underlying, non-swelling polymer of the base member 412. In an example, the intermediate member 350 includes Pur-Sil® and is dip or otherwise coated onto an outer surface of the base member 412. In an example, the intermediate member 350 includes a polyurethane configured to absorb about 10% to about 500% water, such as Tecophilic® urethanes or Tecophilic® solution grade urethanes.

In certain examples, the implant body 402 can include a cavity 416 disposed near the proximal end 418 of the first portion 304. In an example, the first cavity 416 extends inward about 2 millimeters or less from the proximal end 418, and houses a first drug-releasing or other agent-releasing drug supply 420 to provide a sustained drug or other agent release to an eye 100 (FIG. 2). In various examples, the drug supply 420 stores and slowly dispenses an agent to the eye 100 as they are leached out, for example, by tear film fluid. In an example, the drug supply 420 includes a plurality of therapeutic agent inclusions 452, which can be distributed in a matrix 454. In an example, the inclusions 452 comprise a concentrated form of the therapeutic agent (e.g., a crystalline agent form). In an example, the matrix 454 comprises a silicone matrix or the like, and the distribution of inclusions 452 within the matrix are homogeneous or non-homogeneous. In an example, the agent inclusions 452 include droplets of oil, such as Latanoprost oil. In still another example, the agent inclusions 452 include solid particles, such as Bimatoprost particles in crystalline form. The inclusions can be of many sizes and shapes. For instance, the inclusions can include microparticles having dimensions on the order of about 1 micrometer to about 100 micrometers.

In the example shown, the drug supply 420 includes a sheath body 456 disposed over at least a portion thereof such as to define at least one exposed surface 458 of the drug supply. In an example, the sheath body 456 comprises polyimide. The exposed surface 458 can be located at or near the proximal end 418 of the implant body 402 such as to contact a tear or a tear film fluid and release the therapeutic agent at one or more therapeutic levels over a sustained time period when the lacrimal implant 300 is inserted into a lacrimal punctum 212, 214. Further discussion regarding configuring and manufacturing of the drug supply 420 can be found in commonly-owned DeJuan et al., U.S. patent application Ser. No. 11/695,537, entitled "DRUG DELIVERY METHODS, STRUCTURES, AND COMPOSITIONS FOR NASOLACRIMAL SYSTEM," which is herein incorporated by reference in its entirety.

In certain examples, the expandable retention member can include a second drug-releasing or other agent-releasing drug supply 460 to provide a sustained drug or other agent release to one or both of a wall of a lacrimal canaliculus 208, 210 or a nasolacrimal system. The drug supply 460 can be configured to store and slowly dispense an agent after contact with lacrimal fluid within a lacrimal canaliculus 208, 210. In an example, the agent included in the expandable retention member can comprise medicaments, therapeutic agents, or antimicrobials (e.g., silver).

Figure 4C:
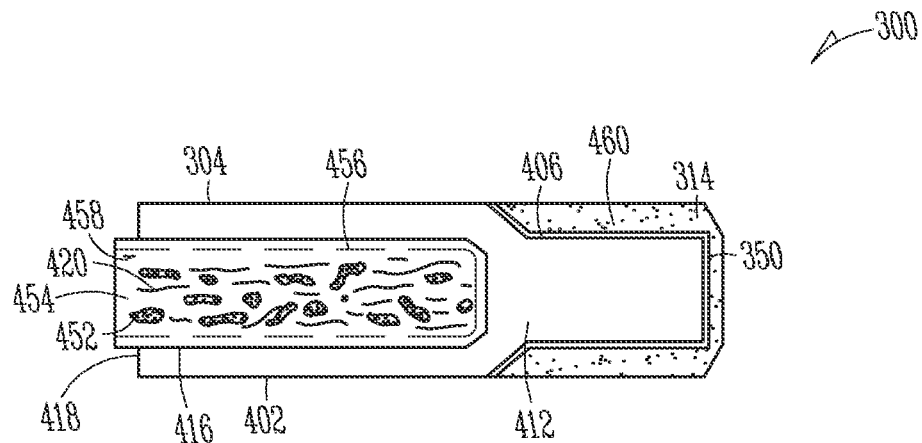
FIG. 4C illustrates another example of a cross-section view of a present lacrimal implant taken along a line parallel to a longitudinal axis of the implant.

FIG. 4C illustrates an example of a cross-sectional view of a lacrimal implant 300 taken along a line parallel to a longitudinal axis of the implant. As shown in FIG. 4B, some of the present lacrimal implants 300 are configured to include a feedback or other projection 422 at or near a proximal end 418 for inhibiting or preventing the lacrimal implant 300 from passing completely within the canalicular lumen, and others are configured to be inserted completely below the punctal opening 212, 214. As shown in FIG. 4C, the lacrimal implant 300 comprises an implant body 402 without a feedback or other projection 322 (FIG. 3A) at or near a proximal end 418 of a first implant body portion 304. Accordingly, the lacrimal implant 300 can, in some examples, be completely inserted within the canalicular lumen.

Figure 5:
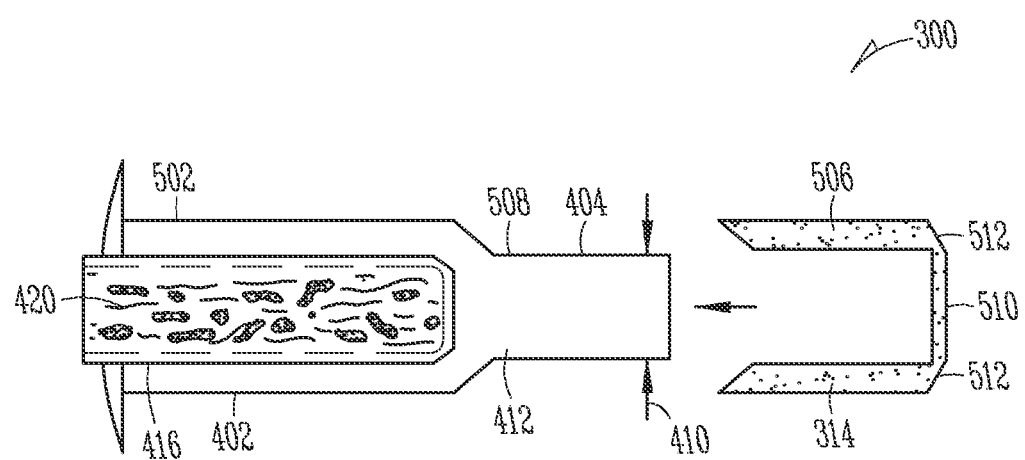
FIG. 5 illustrates an example of an assembly of a present lacrimal implant, which is configured to be retained within a lacrimal punctum and canalicular anatomy.

FIG. 5 illustrates an example of an assembly of a present lacrimal implant 300. As discussed, the lacrimal implant 300 can include a unitary implant body 402 sized to at least partially pass through a lacrimal punctum 212, 214 (FIG. 2) and be positioned within a lacrimal canaliculus 208, 210 (FIG. 2). The implant body 402 can extend from a proximal end portion 502 to a distal end portion 504. In the example shown, the proximal end portion 502 includes a cavity 416 and the distal end portion 504 includes a base member 412 having a diameter 410 less than a diameter of the proximal end portion 502. In an example, a drug core 420 can be included in the cavity 416 and configured to provide a release of an agent to an eye. In various examples, an expandable retention member 314 can be coupled at least partially over the base member 412 and includes a "dry or dehydrated" material hydratable by lacrimal or other fluid to swell from a first diameter to a second diameter greater than the first diameter.

The base member 412 can be coupled with the expandable retention member 314 in a variety of ways. In an example, as shown in FIG. 5, a preformed, swellable (e.g., hydrogel) sleeve 506 can be slid over an outer surface 508 of the base member 412. In an example, the expandable retention member 314 can be dip or otherwise coated onto the base member 412. In an example, a first polymer-based (e.g., urethane-based) base member 412 and a first polymer-based (e.g., urethane-based) expandable retention member 314 can be injection molded concurrently (e.g., via bi-injection molding), thereby allowing the lacrimal implant 300 to be formed in a minimum number of steps. In an example, a multi-shot molding process can be used, which involves sequential injection of separate materials into different locations in a mold. In an example, an insert over-molding process can used such that the base member 412 is first molded then placed into a second mold for over-molding with a polymer for the expandable retention member 314. In various examples, the expandable retention member 314 may extend along any desired length portion of the implant body 402.

In certain examples, one or both of the distal body portion 504 or a distal end 510 of the expandable retention member 314 can include a taper 512 to self-dilate anatomical tissue, such one or both of a lacrimal punctum 212, 214 (FIG. 2) or associated lacrimal canaliculus 208, 210, to a sufficient diameter as the lacrimal implant 300 is being implanted. In this way, the lacrimal implant 300 can be implanted in various size ocular anatomies without the need for pre-dilation via a separate enlarging tool. The taper 512 can be formed so as to not be traumatic to an inner lining of the lacrimal punctum 212, 214 or the lacrimal canaliculus 208, 210.

As shown, the taper 512 can generally narrow from a location near an intermediate portion of the swellable sleeve 506 to the distal end 510 of the sleeve 506, such as from a diameter of about 0.5 millimeters to a diameter of about 0.1 millimeters or less. Among other factors, a determination of a desirable taper 512 for a given implant situation can be made by balancing implant properties, such as a implant body 402 strength desirable for implant insertion with a desire to have a soft, flexible and conforming implant body (e.g., to conform to a lacrimal canaliculus anatomy) upon implantation. In some examples, a lubricious coating disposed on, or impregnated in, one of both of an outer surface of the implant body 402 or an outer surface of the expandable retention member 314 can be used to further aid insertion of the lacrimal implant 300 into the anatomical tissue. In an example, the lubricious coating can include a silicone lubricant. In an example, the outer surface of the implant body 402 or the expandable retention member 314 can be treated via plasma or radiation in order to securely bond a thin coating of lubricious material (e.g., hydrogel).

In various examples, the outer surface of one or both of the implant body 402 or the expandable retention member 314 can be formed, or surface treated to be, generally smooth to inhibit bacteria from attaching to the lacrimal implant 300 and incubating. The generally smooth outer surface can also prevent damage to the inner lining of the receiving anatomical tissue, such as a lacrimal punctum 212, 214 (FIG. 2) or the associated lacrimal canaliculus 208, 210 (FIG. 2), during implantation. As further discussed in commonly-owned Rapacki, U.S. patent application Ser. No. 12/283,002, entitled "SURFACE TREATED IMPLANTABLE ARTICLES AND RELATED METHODS," which is herein incorporated by reference in its entirety and which claims priority in part to U.S. Patent Application No. 61/057, 246, the outer surface of the plug body 402, for instance, can be improved via a polishing procedure using dichloride methane or other suitable media in conjunction with a tumbling process.

In some examples, an antimicrobial coating can be disposed on, or impregnated in, at least a portion of the outer surface of one or both of the implant body 402 or the expandable retention member 314 to further prevent bacteria growth on the implant body. In an example, the antimicrobial coating can include an agent selected from the group consisting of 2-bromo-2-nitropropane-1,3-diol, 5-bromo-5-nitro-1,3-dioxane, 7-ethyl bicyclooxazolidine, benzalkonium chloride, benzethonium chloride, benzoic acid, benzyl alcohol, boric acid, bronopol, cetylpyridinium chloride, chlorhexidine digluconate, chloroacetamide, chlorobutanol, chloromethyl isothiazolinone and methyl isothiazoline, dimethoxane, dimethyl oxazolidine, dimethyl hydroxymethyl pyrazole, chloroxylenol, dehydroacetic acid, diazolidinyl urea, dichlorobenzyl alcohol, DMDM hydantoin, ethyl alcohol, formaldehyde, glutaraldehyde, hexachlorophene, hexetidine, hexamethylenetramine, imidazolidinyl urea, iodopropynyl butylcarbamate, isothiazolinones, methenammonium chloride, methyldibromo glutaronitrile, MDM hydantoin, minocycline, ortho phenylphenol, p-chloro-m-cresol, parabens (butylparaben, ethylparaben, methylparaben), phenethyl alcohol, phenoxyethanol, piroctane olamine, polyaminopropyl biguanide, polymethoxy bicyclic oxazolidine, polyoxymethylene, polyquaternium-42, potassium benzoate, potassium sorbate, propionic acid, quaternium-15, rifampin, salicylic acid, selenium disulfide, sodium borate, sodium iodate, sodium hydroxymethylglycinate, sodium propionate, sodium pyrithione, sorbic acid, thimerosal, triclosan, triclocarban, undecylenic acid, zinc phenosulfonate, and zinc pyrithione. In an example, the antimicrobial coating can include a material selected from the group consisting of silver lactate, silver phosphate, silver citrate, silver acetate, silver benzoate, silver chloride, silver iodide, silver lodate, silver nitrate, silver sulfadiazine, silver palmitate or one or more mixtures thereof. In an example, the antimicrobial coating can include at least one of an antibiotic or an antiseptic. For instance, the antimicrobial coating can include a temporary anesthetic lasting, on average, between a few hours and a day. In still other examples, the antimicrobial coating can include a drug use to treat an underlying disease, such as a bolus for immediate effect.

Figure 6:
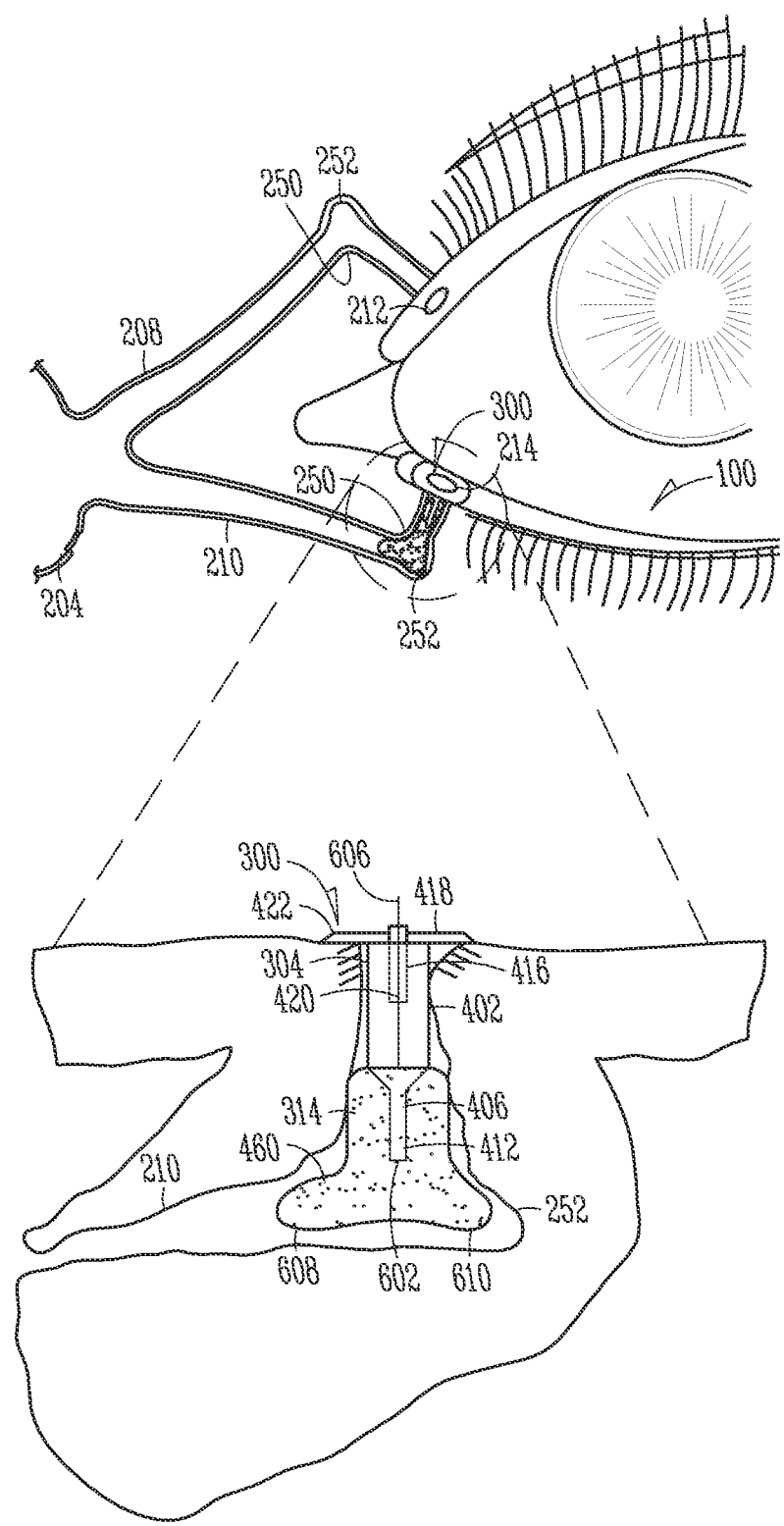
FIG. 6 illustrates an example of a schematic view of a present lacrimal implant, which is retained within a lacrimal punctum and canalicular anatomy.

FIG. 6 illustrates an example of a schematic view of a lacrimal implant 300 implanted in a lower lacrimal punctum 214 and associated canaliculus 210. In some examples, a lacrimal implant 300 can be implanted in an upper lacrimal punctum 212 and associated canaliculus 208. In this example, the lacrimal implant 300 comprises a implant body 402, including first 304 and second 406 portions, which is sized and shaped for at least partial insertion into the lacrimal punctum 214. The first portion 304 is formed from a polymer and includes a first diameter 408 (FIG. 4B). The second portion 406 is also formed from a polymer and includes a base member 412 (e.g., mandrel or spine-like member) having a second diameter 410 (FIG. 4B) less than the first diameter 408. An expandable retention member 314, such as a swellable material, can be bonded or otherwise coupled over the base member 412 such that it envelops, at least in part, a portion of the base member 412. In certain examples, an outer surface of one or both of the implant body 402 or the expandable retention member 314 can include grooves or a coating of a wicking material such as to allow fluid flow around the implant body 402.

As shown, the first portion 304 of the implant body 402 can be configured to rest, at a proximal end 418, against the punctal opening 214 and rest, at a distal end 602, within the associated lacrimal canaliculus 210. In this example, an integral feedback or other projection 422 extending around the proximal end 418 inhibits or prevents the lacrimal implant 300 from passing completely within the canalicular lumen 210.

As further shown, the second portion 406, including the base member 412 at least partially enveloped by the expandable retention member 314, can be configured to rest and retain the lacrimal implant 300 within the associated lacrimal canaliculus 210. As the expandable retention member absorbs or otherwise retains lacrimal or other fluid, such as upon insertion into the lacrimal punctum 214, its size increases radially or longitudinally and its shape may change thereby urging itself against and slightly biasing a wall of the associated canaliculus 210, while still being comfortable to the subject. In an example, a longitudinal swelling direction of the expandable retention member 314 extends laterally relative to a longitudinal axis 606 of the implant body 402. In an example, a portion 608 of the expandable retention member 314 is configured to at least partially extend toward a horizontal section of the lacrimal canaliculus 210. In an example, a portion 610 of the expandable retention member 314 is configured to at least partially extend toward an ampulla 252 of the lacrimal canaliculus 210. In an example, the swellable material of the expandable retention member 314 can comprise a hydrogel having a water content, at a fully hydrated state, of about 500% to about 2000% by weight and, at a "dry or dehydrated" state, of less than about 10%, such as about 1%. In certain examples, the expandable retention member 314 is configured to allow for an expansion capacity of up to about one times its "dry or dehydrated" volume, up to about five times its "dry or dehydrated" volume, or up to about ten times its "dry or dehydrated" volume.

Forceps or another insertion tool can be used to insert the lacrimal implant 300 in a lacrimal punctum 212, 214 and the associated canaliculus 208, 210. In various examples, the second portion 406 of the implant body 402 can be advanced into the depth of a lacrimal canaliculus 208, 210 by manipulation of the inserter tool until a feedback or other projection 422, if present, is seated against the punctal opening 212, 214. When it is desired to remove the lacrimal implant 300, the projection 432 can be readily grasped with the forceps, for example, and withdrawn from the punctal opening 212, 214. It is believed the insertion and removal processes associated with the present lacrimal implants 300 may, in some instances, be simply performed in a short amount of time by a general ophthalmologist in his/her office without the need for special skills or expensive equipment. In some instances, after a first lacrimal implant has been removed, a second lacrimal implant including a supply of an agent is inserted into the subject until he/she no longer requires treatment.

In certain examples, the implant body 402 can include a cavity 416 disposed near the proximal end 418 of the first portion 304. In this example, the first cavity 418 extends inward from the proximal end 418 and includes a first drug-releasing or other agent-releasing drug supply 420. The lacrimal implant 300 can be oriented with the expandable retention member 314 aligned for placement in a lacrimal canaliculus 208, 210, while the drug supply 420 and the proximal end 418 are substantially aligned with the exterior of the punctum openings 212, 214 to provide a sustained drug or other agent release to an eye 100 (e.g., to treat an infection, inflammation, glaucoma or other ocular disease or disorder). The drug or other agent release can occur, at least in part, via an exposed surface of the drug supply 420. In this example, the exposed surface of the drug supply 420 can be positioned above the proximal end 418 such that the drug supply 420 at least partially protrudes outside of the implant body 402.

In certain examples, the expandable retention member can include a second drug-releasing or other agent-releasing drug supply 460 to provide a sustained drug or other agent release to one or both of a wall of a lacrimal canaliculus 208, 210 or a nasolacrimal system. The drug supply 460 can be configured to store and slowly dispense an agent after contact with lacrimal fluid within a lacrimal canaliculus 208, 210. In an example, the agent included in the expandable retention member can comprise medicaments, therapeutic agents, or antimicrobials (e.g., silver).

FIGS. 7A-7G illustrate examples of lacrimal implants 300 that can be insertable into a lacrimal punctum 212, 214 (FIG. 2). The insertion of the lacrimal implants 300 into a lacrimal punctum 212, 214 can allow for one or more of inhibition or blockage of tear flow through a lacrimal canaliculus 208, 210 (FIG. 2) (e.g., to treat dry eyes), or the sustained delivery of a therapeutic agent to an eye (e.g., to treat an infection, inflammation, glaucoma or other ocular diseases or disorders) or nasal passage (e.g., to treat a sinus or allergy disorder).

In various examples, the lacrimal implants 300 comprises an implant body 402, including first 304 and second 406 portions, which is sized and shaped for at least partial insertion into a lacrimal punctum 212, 214. The first portion 304 is formed from a polymer and includes a first diameter 408 (FIG. 4B). The second portion 406 is also formed from a polymer and includes a base member 412 (e.g., mandrel or spine-like member) having a second diameter 410 (FIG. 4B) less than the first diameter 408. In some examples, such as are shown in FIGS. 7A-7D, the first 304 and second 406 portions are integrally coupled and comprise a unitary implant body 402. In some examples, such as are shown in FIGS. 7E-7G, the first 304 and second 406 portions are separate elements, which can be coupled to one another via an engagement between a coupling void and a coupling arm, for instance. In various examples, the base member 412 can include one or more arm members 702 protruding from an outer surface 508 thereof.

An expandable retention member 314, such as a swellable material, can be bonded or otherwise coupled over the base member 412 such that it envelops, at least in part, a portion of the base member 412. In an example, the expandable retention member substantially envelops the base member 412. The one or more arm members 702 increase the surface area for bonding or other coupling between one or more of the expandable retention member 314, an intermediate member 350 (FIG. 4B), and the base member 412. The expandable retention member 314, for example, would will the spaces between the one or more arm members 702 upon application. As the expandable retention member 314 absorbs or otherwise retains lacrimal or other fluid, such as upon insertion into a lacrimal punctum 212, 214, its size increases and its shape may change thereby urging itself against and slightly biasing a wall of the associated canaliculus 208, 210.

Figure 7A:
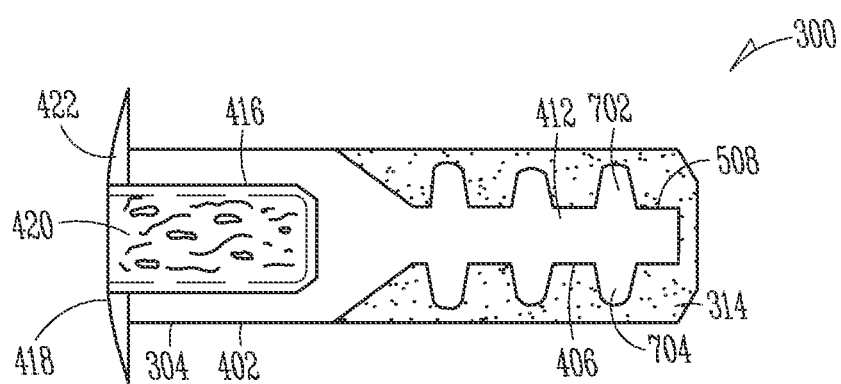
FIGS. 7A-7G illustrate examples of cross-sectional views of other present lacrimal implants, each of which is configured to be retained within a lacrimal punctum and canalicular anatomy.

In the example of FIG. 7A, the lacrimal implant 300 includes a unitary implant body 402 extending from a first portion 304 to a second portion 406. The first portion 304 can include a cavity 416 disposed near a proximal end 418 of the first portion 304. The cavity 416 can include a first drug-releasing or other agent-releasing drug supply 420 to provide a sustained drug or other agent release to an eye. The implant body 402 can further include an integral feedback or other, projection 422 extending laterally at least partially from or around the proximal end 318. In various examples, the projection 422 can be configured to seat against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position.

As shown, the second portion 406 can include a base member 412 (e.g., mandrel or spine-like member) having a diameter 410 (FIG. 4B) less than a diameter 408 (FIG. 4B) of the first portion 304. In this example, the base member 412 includes one or more arm members 702 in the form of ribs 704. Each rib 704 can include a curved or non-curved projection extending from an outer surface of the base member 412, such as projecting laterally relative to a longitudinal axis of the base member 412. In this example, three pairs of ribs 704 extend from the base member 412; however, more and fewer than three pairs of ribs 704 may also be used without departing from the scope of the present subject matter. The ribs 704 can provide strength to the lacrimal implant 300 by increasing the surface area to which one or both of the expandable retention member 314 or an intermediate member 350 (FIG. 4B) are coupled to the base member 412.

Figure 7B:
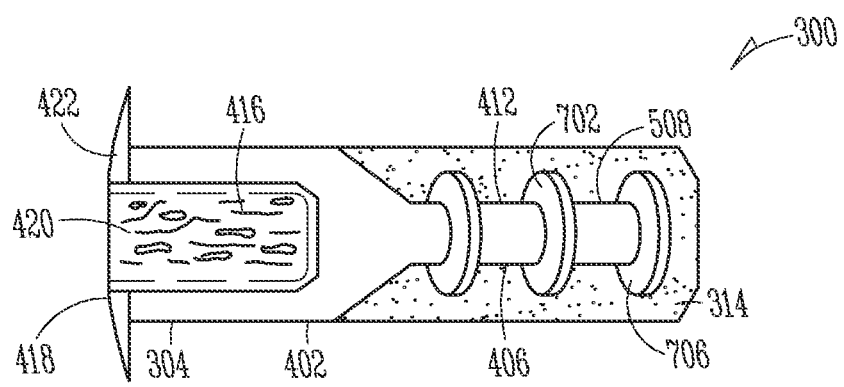

In the example of FIG. 7B, the lacrimal implant 300 includes a unitary implant body 402 extending from a first portion 304 to a second portion 406. The first portion 304 can include a cavity 416 disposed near a proximal end 418 of the first portion 304. The cavity 416 can include a first drug-releasing or other agent-releasing drug supply 420 to provide a sustained drug or other agent release to an eye. The implant body 402 can further include an integral feedback or other projection 422 extending laterally at least partially from or around the proximal end 418. In various examples, the projection 422 can be configured to sit against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position.

As shown, the second portion 406 can include a base member 412 (e.g., mandrel or spine-like member) having a diameter 410 (FIG. 4B) less than a diameter 408 (FIG. 4B) of the first portion 304. In this example, the base member 412 includes one or more arm members 702 in the form of disks 706. Each disk 706 can include a relatively flat top or bottom surface and can include a greater cross-sectional size than an adjacent portion of the base member 412. The one or more disks 706 can be spaced apart along a longitudinal axis of the base member 412 and extend from an outer surface of the base member 412. In an example, three disks 706 extend from base member 412; however, more and fewer than three disks 706, such as one disk 706, may also be used without departing from the scope of the present subject matter. The disks 706 can provide strength to the lacrimal implant 300 by increasing the surface area to which one or both of the expandable retention member 314 or an intermediate member 350 (FIG. 4B) are coupled to the base member 412.

Figure 7C:
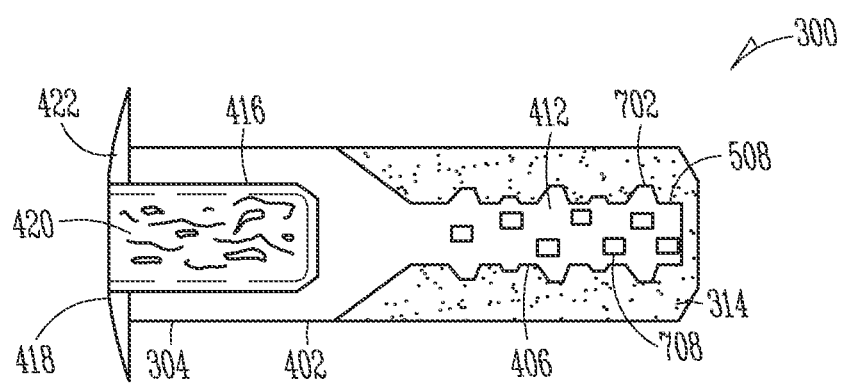

In the example of FIG. 7C, the lacrimal implant 300 includes a unitary implant body 402 extending from a first portion 304 to a second portion 406. The first portion 304 can include a cavity 416 disposed near a proximal end 418 of the first portion 304. The cavity 416 can include a first drug-releasing or other agent-releasing drug supply 420 to provide a sustained drug or other agent release to an eye. The implant body 402 can further include an integral feedback or other projection 422 extending laterally at least partially from or around the proximal end 418. In various examples, the projection 422 can be configured to seat against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position.

As shown, the second portion 406 can include a base member 412 (e.g., mandrel or spine-like member) having a diameter 410 (FIG. 4B) less than a diameter 408 (FIG. 4B) of the first portion 304. In this example, the base member 412 includes one or more arm members 702 in the form of spikes 708. Each spike 708 can protrude radially outward from an outer surface of the base member 412 at any location around a circumference of the base member 412. In an example, six or more spikes 708 extend from base member 412; however, fewer than six spikes 708 may also be used without departing from the scope of the present subject matter. The spikes 708 can provide strength to the lacrimal implant 300 by increasing the surface area to which one or both of the expandable retention member 314 or an intermediate member 350 (FIG. 4B) are coupled to the base member 412.

Figure 7D:
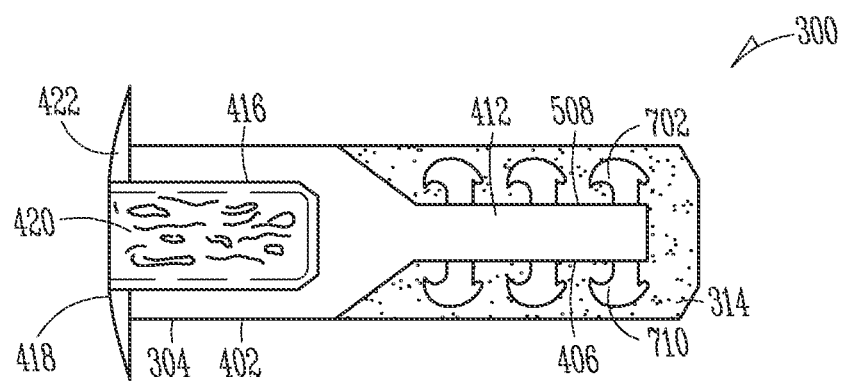
Figure 7E:
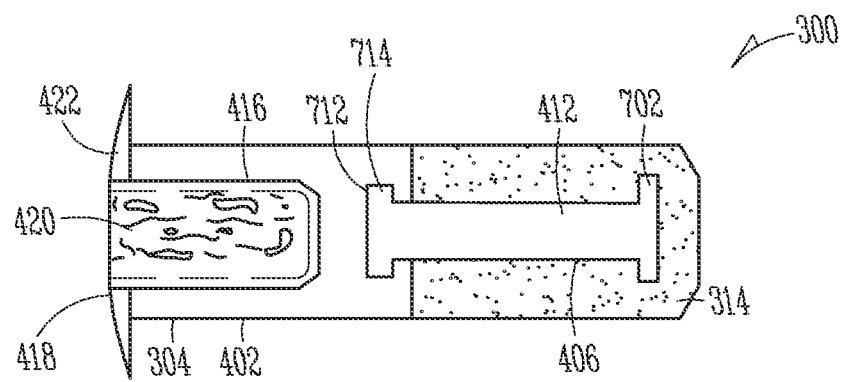
Figure 7F:
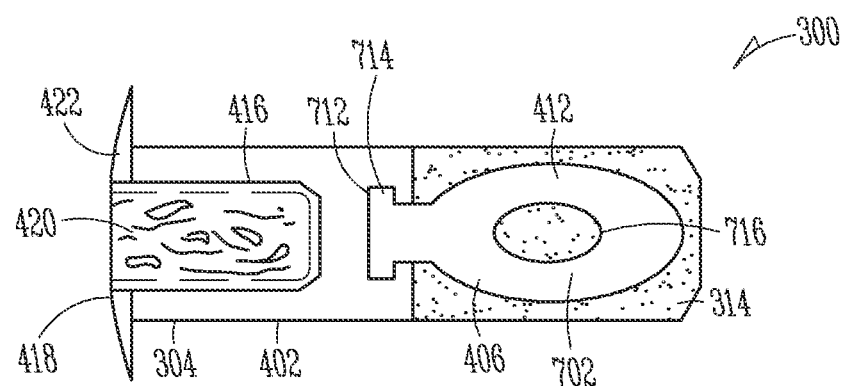
Figure 7G:
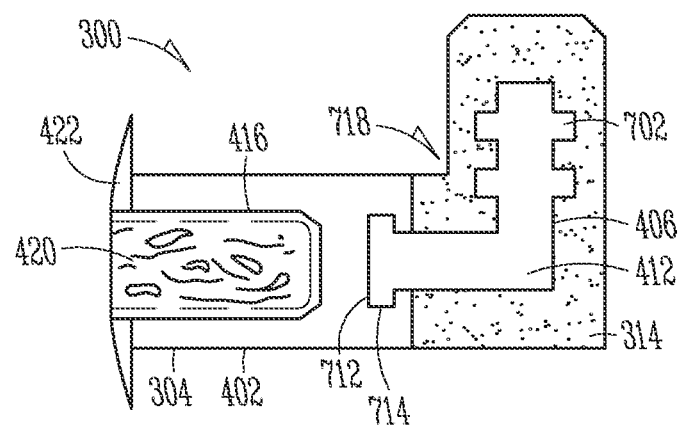

In the example of FIG. 7D, the lacrimal implant 300 includes a unitary implant body 402 extending from a first portion 304 to a second portion 406. The first portion 304 can include a cavity 416 disposed near a proximal end 418 of the first portion 304. The cavity 416 can include a first drug-releasing or other agent-releasing drug supply 420 to provide a sustained drug or other agent release to an eye. The implant body 402 can further include an integral feedback or other projection 422 extending laterally at least partially from or around the proximal end 418. In various examples, the projection 422 can be configured to sit against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position.

As shown, the second portion 406 can include a base member 412 (e.g., mandrel or spine-like member) having a diameter 410 (FIG. 4B) less than a diameter 408 (FIG. 4B) of the first portion 304. In this example, the base member 412 includes one or more arm members 702 having a curved shape, such as a fish hook-like shape 710. Each fish hook-like projection 710 can protrude radially outward from an outer surface of the base member 412 at any location around a circumference of the base member 412. In an example, at least one of the fish hook-like projections include a barb or other backward pointing ridge. In this example, three pairs of fish hook-like projections 710 extend from the base member 412; however, more and fewer than three pairs of fish hook-like projections 710 may also be used without departing from the scope of the present subject matter. The fish hook-like projections 710 or other curved shaped projections can provide strength to the lacrimal implant 300 by increasing the surface area to which one or both of the expandable retention member 314 or an intermediate member 350 are coupled to the base member 412.

In the example of FIGS. 7E and 7G, the lacrimal implant 300 includes a implant body 402 comprising first 304 and second 406 separable portions, which can be coupled to one another via an engagement between a coupling void 712 and a coupling arm 714, for instance. In an example, a polymer forming the first portion 304, such as a silicone-based material, is different than a polymer forming the second portion 406, such as a polyester, silk, polycarbonate, urethane-based material or other material having a melting temperature higher than that at which the polymer of the first portion 304 is cured or having a greater hardness. The first portion 304 can include a cavity 416 disposed near a proximal end 418 of the first portion 304. The cavity 416 can include a first drug-releasing or other agent-releasing drug supply 420 to provide a sustained drug or other agent release to an eye. The implant body 402 can further include an integral feedback or other projection 422 extending laterally at least partially from or around the proximal end 418. In various examples, the projection 422 can be configured to sit against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position.

As shown, the second portion 406 can include a base member 412 (e.g., mandrel or spine-like member) comprising a variety of shapes and having a diameter 410 (FIG. 4B) less than a diameter 408 of the first portion 304. In these examples, the base member 412 includes one or more arm members 702 extending from an outer surface of the base member 412, such as projecting laterally relative to a longitudinal axis of the base member 412, which, in the example of FIG. 7E, coincides with a longitudinal axis of the first portion 304 and, in the example of FIG. 7G, is angled 718 relative to the axis of the first portion 304. In an example, the angled 718 intersection between the longitudinal axis of the base member 412 and the longitudinal axis of the first portion 304 is formed upon or after implantation of the implant body 402 into a lacrimal canaliculus 208, 210. The one or more arm members 702 can provide strength to the lacrimal implant 300 by increasing the surface area to which one or both of the expandable retention member 314 or an intermediate member 350 (FIG. 4B) are coupled to the base member 412.

In the example of FIG. 7F, the lacrimal implant 300 includes an implant body 402 comprising first 304 and second 406 separable portions, which can be coupled to one another via an engagement between a coupling void 712 and a coupling arm 714, for instance. In an example, a polymer forming the first portion 304, such as a silicone-based material, is different than a polymer forming the second portion 406, such as a polyester, silk, polycarbonate, urethane-based material or other material having a melting temperature higher than that at which the polymer of the first portion 304 is cured or having a greater hardness. The first portion 304 can include a cavity 416 disposed near a proximal end 418 of the first portion 304. The cavity 416 can include a first drug-releasing or other agent-releasing drug supply 420 to provide a sustained drug or other agent release to an eye. The implant body 402 can further include an integral feedback or other projection 422 extending laterally at least partially from or around the proximal end 418. In various examples, the projection 422 can be configured to sit against or near a punctal opening 212, 214 when the second portion 406 of the implant body 402 is positioned within the associated canalicular lumen 208, 210, such as for inhibiting or preventing the lacrimal implant 300 from passing completely within the canalicular lumen, for providing tactile or visual feedback information to an implanting user (e.g., as to whether the implant is fully implanted), or for removing the lacrimal implant 300 from an implant position.

As shown, the second portion 406 can include a base member 412 (e.g., mandrel or spine-like member) having a diameter 410 (FIG. 4B) less than a diameter 408 (FIG. 4B) of the first portion 304. In this example, the base member 412 includes one or more arm members 702 extending from an outer surface of the base member 412, such as projecting in a balloon-like shape from a juncture between the coupling void 712 and the coupling arm 714. In an example, the one or more arm members 702 include one or more voids 616 sized to receive a portion of the expandable retention member 314 or an intermediate member 350. The one or more arm members 702 can provide strength to the lacrimal implant 300 by increasing the surface area to which one or both of the expandable retention member 314 or an intermediate member 350 (FIG. 4B) are coupled to the base member 412.

Figure 8:
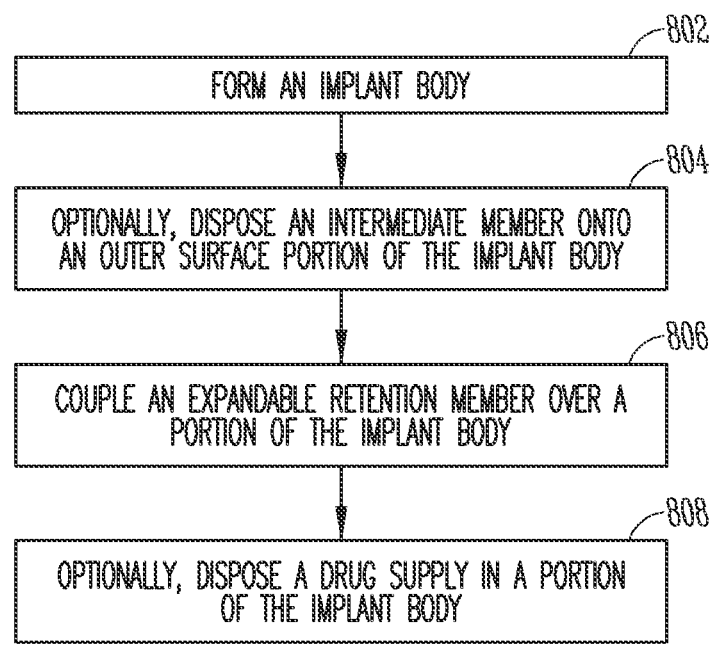
FIG. 8 illustrates an example of a method of manufacturing a present lacrimal implant, which is configured to be retained within a lacrimal punctum and canalicular anatomy.

FIG. 8 is a block diagram illustrating an example of a method 800 of manufacturing a lacrimal implant configured to be at least partially insertable into a lacrimal punctum. At 802, a implant body, including first and second portions, is formed. Forming the first portion can include melt, molding or otherwise processing a polymer into a shape having a first diameter. Forming the second portion can include melt, molding or otherwise processing a polymer into a base member shape having a second diameter less than the first diameter. In an example, forming the first portion, the second portion, or both can include injection molding using respectively a melt of the first polymer, the second polymer, or both polymers. Polyurethane polymers and copolymers are adapted for melt processing, thus avoiding both the added complexity of solvent casting technology, the cost of dealing with the necessary solvents, and the possibility of residual solvents in the polymeric materials of the implant. In an example, forming the implant body further includes forming a cavity extending inward form a proximal end of the first portion. In an example, forming the implant body further includes forming one or more arm members protruding laterally from an outer surface of the base member. In some examples, the implant body is formed from a urethane-based material, such as polyurethane. In some examples, the implant body is formed from a silicone material. Optionally, one or more portions of an outer surface of the base member are plasma treated to encourage coupling to a covering element.

At 804, an intermediate member is optionally disposed on the outer surface of the base member. In various examples, the intermediate member includes a third polymer configured to absorb a greater amount of fluid (e.g., lacrimal fluid) than a polymer of the implant body. In an example, the third polymer can be incorporated into the lacrimal implant as a melt. In an example, the intermediate member can be applied to the base member using an injection molding process, or it can be applied using a solvent-dip coating process. For instance, the dip-coating process can be used to apply a thin layer of the intermediate member onto the outer surface of the base member.

At 806, an expandable retention member is coupled at least partially over the base member, and optionally, the intermediate member. In an example, the expandable retention member is coupled over the base member such that the base member is entirely or substantially surrounded. In various examples, the expandable retention member includes a polymer configured to absorb a greater amount of fluid than both the implant body and the intermediate member. In an example, the expandable retention member includes a urethane-based material, such as urethane-based hydrogel, and is molded over the base member, which can also include a urethane-based material. In an example, the expandable retention member is formed using an injection molding process. For instance, a urethane-based base member and a urethane-based expandable retention member could be melted and injected into a mold through two separate mold ports, such as is performed in a multi-shot molding process. In another example, either the base member or the expandable retention member could be molded individually, then the other element could be injected into the remaining portion of the mold, such as is performed in an insert over-molding process. In an example, the expandable retention member is dip coated onto an outer surface of the base member. In an example, the expandable retention member includes a hydrogel sleeve (e.g., hydrogel tubing) configured to slide onto the outer surface of the base member and be coupled using, for instance, a urethane-based adhesive such as Tecoflex® 1-MP.

At 808, a drug supply is disposed in the cavity of the first body portion. In various examples, the drug supply stores and slowly dispenses an agent to the eye as they are leached out, for example, by tear film fluid. The drug or other agent release can occur, at least in part, via an exposed surface of the drug supply. In an example, the exposed surface of the drug supply can be positioned above the proximal end such that the drug supply at least partially protrudes outside of the implant body. In some examples, the exposed surface of the drug supply can be flush or slightly below the proximal end such that the drug supply does not protrude outside of the implant body.

The lacrimal implant can also be made by processes including insert overmolding where the implant body can be molded out of one material and once completed can be placed into a second mold where the next material is injected around the part; multi-component molding where there is simultaneous injection of multiple materials into a mold either through the same injection nozzle or separate nozzles; multi-shot molding, where there is sequential injection of separate materials into different locations of the mold; and extrusion of a hydrogel sleeve which is then bonded (via adhesive or melt bonded) to a molded implant body.

Sheath Body Examples:

In various ways, the sheath body surrounding and optionally included in the drug supply can comprise appropriate shapes and materials to control migration of one or agents from the supply. In some examples, the sheath body is configured to be conformable to an implant anatomy, such as an anatomy of a lacrimal punctum or canaliculus. As discussed, in some examples, the sheath body houses the drug supply and can fit snugly against an outer surface of the matrix/agent mixture. The sheath body can be made from a material that is substantially impermeable to the agents so that the rate of migration of the agents is largely controlled by an exposed surface area of the drug supply that is not covered by the sheath body. In many examples, migration of the agents through the sheath body can be about one tenth of the migration of the agent through the exposed surface of the drug supply, or less. Suitable sheath body materials can include, among others, polyimide, polyethylene terephthalate (PET). The sheath body can have a thickness, as defined from the sheath surface adjacent the outer matrix/agent mixture surface to an opposing sheath surface away from the outer surface, of about 0.00025 inches to about 0.0015 inches. The total diameter of the sheath that extends across the drug supply ranges from about 0.2 millimeters to about 1.2 millimeters. The drug supply can be formed by dip coating the matrix in the sheath body. In some examples, the sheath body can comprise a tube into which the matrix/agent mixture is introduced. The sheath body can also be dip coated around the matrix/agent mixture, for example dip coated around a pre-formed matrix/agent core.

The sheath body can be provided with one or more additional features such as to facilitate clinical use of the lacrimal implants discussed herein. For example, the sheath can receive a drug supply that is exchangeable in situ, while the implant body remains implanted in the patient, or after its removal. In some examples, the sheath body can be provided with one or more external protrusions that apply force to the sheath body when squeezed, which cause the matrix/agent mixture to be ejected from the sheath body. A replacement drug supply can then be positioned in the sheath body.

Therapeutic Agent Examples:

A therapeutic agent (or simply "agent") can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Example available agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; antisecretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens,—estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdata.fda.gov/scripts/cder/drugsatfda/index. The present lacrimal implants can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of diseases or disorders that can be treated with above-listed agents include, but are not limited to, glaucoma, pre- and post-surgical ocular treatments, dry eye, anti-eye allergy, anti-infective, post-surgical inflammation or pain, or respiration-related disorders, such as allergies In some examples, the therapeutic agent can include a lubricant or a surfactant, for example a lubricant to treat dry eye. In other examples, the therapeutic agent can include an absorbent capable of absorbing tear from an eye.

Drug Supply Examples:

The drug supply can comprise one or more agents, and in some examples, one or more matrix materials to provide sustained release of the agents. The one or more agents can migrate from an exposed surface of the drug supply to the target tissue (e.g., ciliary muscles of an eye) based, at least in part, on a solubility of the agents in the matrix. The rate of migration of the agents from the exposed surface can also be related to the concentration of agents dissolved in the matrix. In some examples, the concentration of agents dissolved in the drug supply can be controlled to provide the desired release rate of the agents. In addition or in combination, the rate of migration of agents from the exposed surface can be related to one or more properties of the matrix in which the agents dissolve, such as the properties of a silicone matrix formulation. In some examples, the agents included in the drug supply can include liquid, solid, solid gel, solid crystalline, solid amorphous, solid particulate, or dissolved forms. In one such example, liquid Latanoprost droplets or solid Bimatoprost particles are dispersed in a silicone matrix.

The drug supply can comprise one or more biocompatible materials capable of providing a sustained release of the one or more agents. Although the drug supply is primarily discussed above with respect to an example comprising a matrix including a substantially non-biodegradable silicone matrix with dissolvable inclusions of the agents located therein, the drug supply can include other structures that provide sustained release of the agents, for example a biodegradable matrix, a porous drug supply, a liquid drug supply or a solid drug supply. A matrix that includes the agents can be formed from either biodegradable or non-biodegradable polymers. In some examples, a non-biodegradable drug supply can include silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug supply can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug supply can comprise a hydrogel polymer.

EXPERIMENTAL EXAMPLES

In order that the present lacrimal implants can be more fully understood, the following examples are given by way of illustration.

Experimental Example 1

Figure 9:
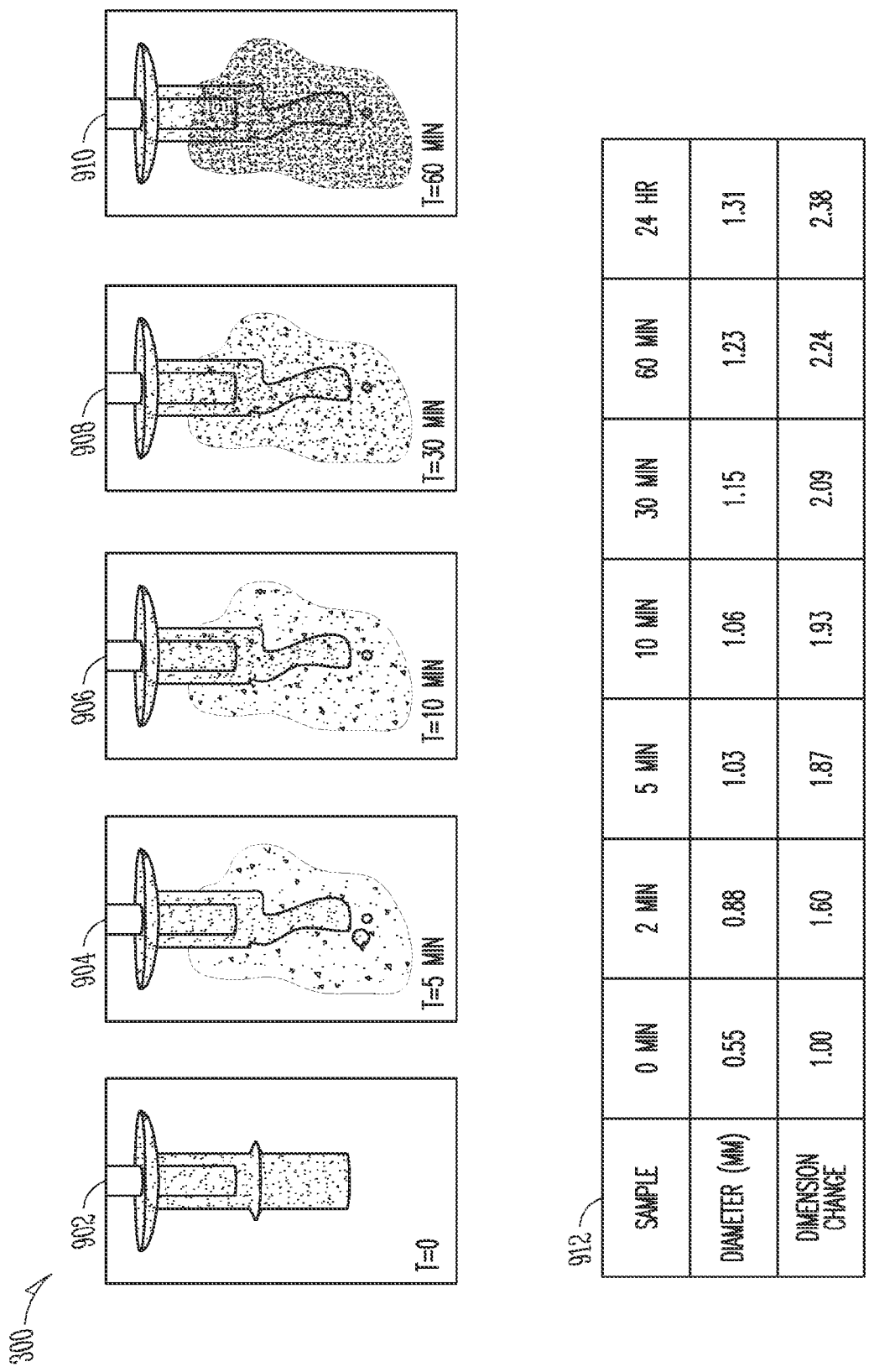
FIGS. 9-12 illustrate and chart example experimental results of a present lacrimal implant, which is configured to be retained within a lacrimal punctum and canalicular anatomy.

FIG. 9 illustrates a lacrimal implant 300 comprising an implant body, which includes a base member, and an expandable retention member coupled at least partially over the base member. In this example, the implant body includes a polyurethane/silicone copolymer and the expandable retention element includes a polyurethane hydrogel sleeve.

The lacrimal implant 300 was tested by soaking in a saline solution and changes to both diameter and length of the expandable retention member were measured. At 902, the implant body and the expandable retention member are shown at t=0 minutes. At 904, the implant body and the expandable retention member are shown at t=5 minutes. At 906, the implant body and the expandable retention member are shown at t=10 minutes. At 908, the implant body and the expandable retention member are shown at t=30 minutes. At 910, the implant body and the expandable retention member are shown at t=5 minutes. Table 912 shows that the expandable retention element increased in dimensional size to 1.23 millimeters (a dimensional change of 2.24 times the original dimension) in 60 minutes, and further increased to 1.31 millimeters (a dimensional change of 2.38 times the original dimension) in 24 hours.

Experimental Example 2

Figure 10:
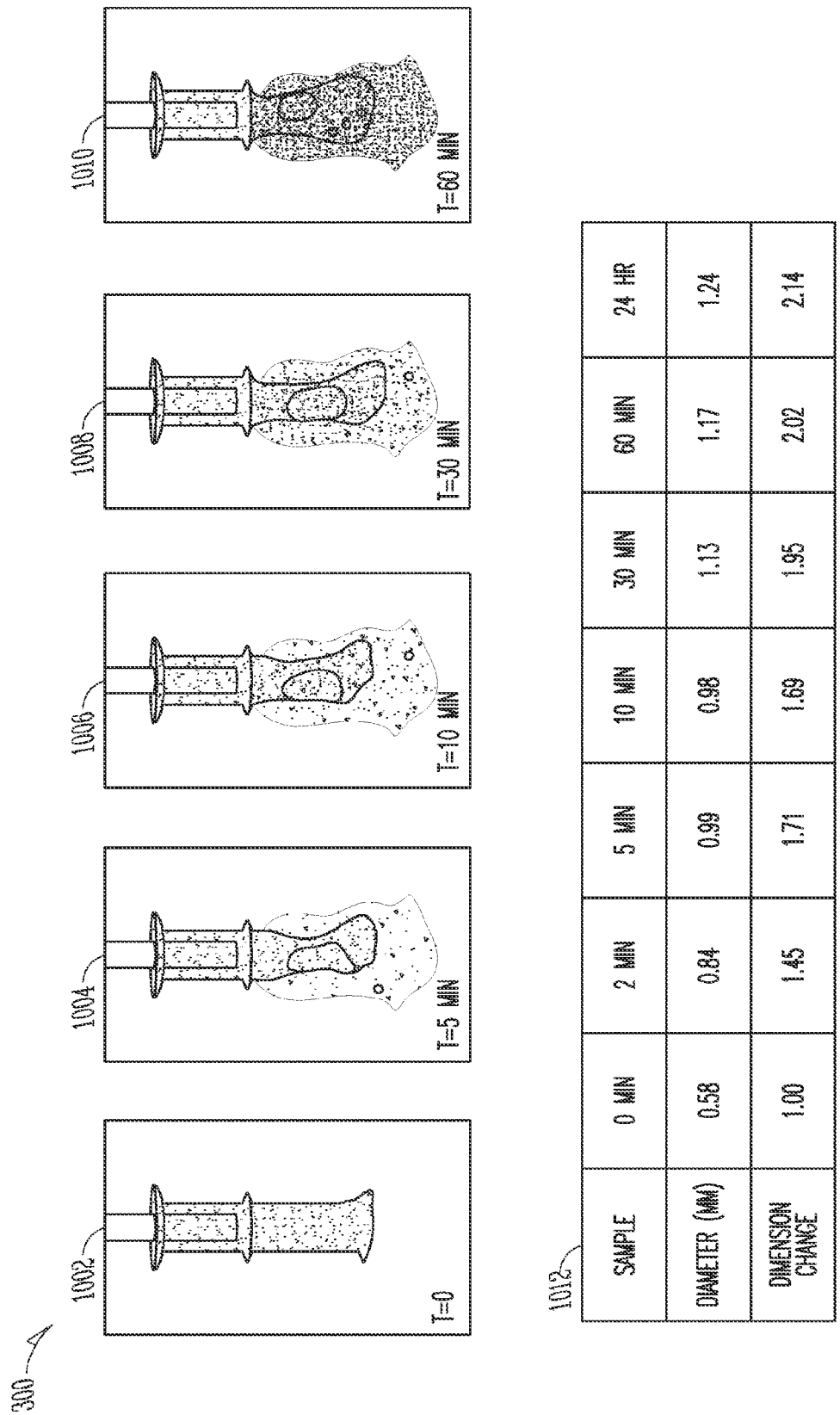

FIG. 10 illustrates a lacrimal implant 300 comprising a implant body, which includes a base member, and an expandable retention member coupled at least partially over the base member. In this example, the implant body includes a polyurethane/silicone copolymer and the expandable retention element includes a polyurethane hydrogel sleeve.

The lacrimal implant 300 was tested by soaking in a saline solution and changes to both diameter and length of the expandable retention member were measured. At 1002, the implant body and the expandable retention member are shown at t=0 minutes. At 1004, the implant body and the expandable retention member are shown at t=5 minutes. At 1006, the implant body and the expandable retention member are shown at t=10 minutes. At 1008, the implant body and the expandable retention member are shown at t=30 minutes. At 1010, the implant body and the expandable retention member are shown at t=5 minutes. Table 1012 shows that the expandable retention element increased in dimensional size to 1.17 millimeters (a dimensional change of 2.02 times the original dimension) in 60 minutes, and further increased to 1.24 millimeters (a dimensional change of 2.14 times the original dimension) in 24 hours.

Experimental Example 3

Figure 11:
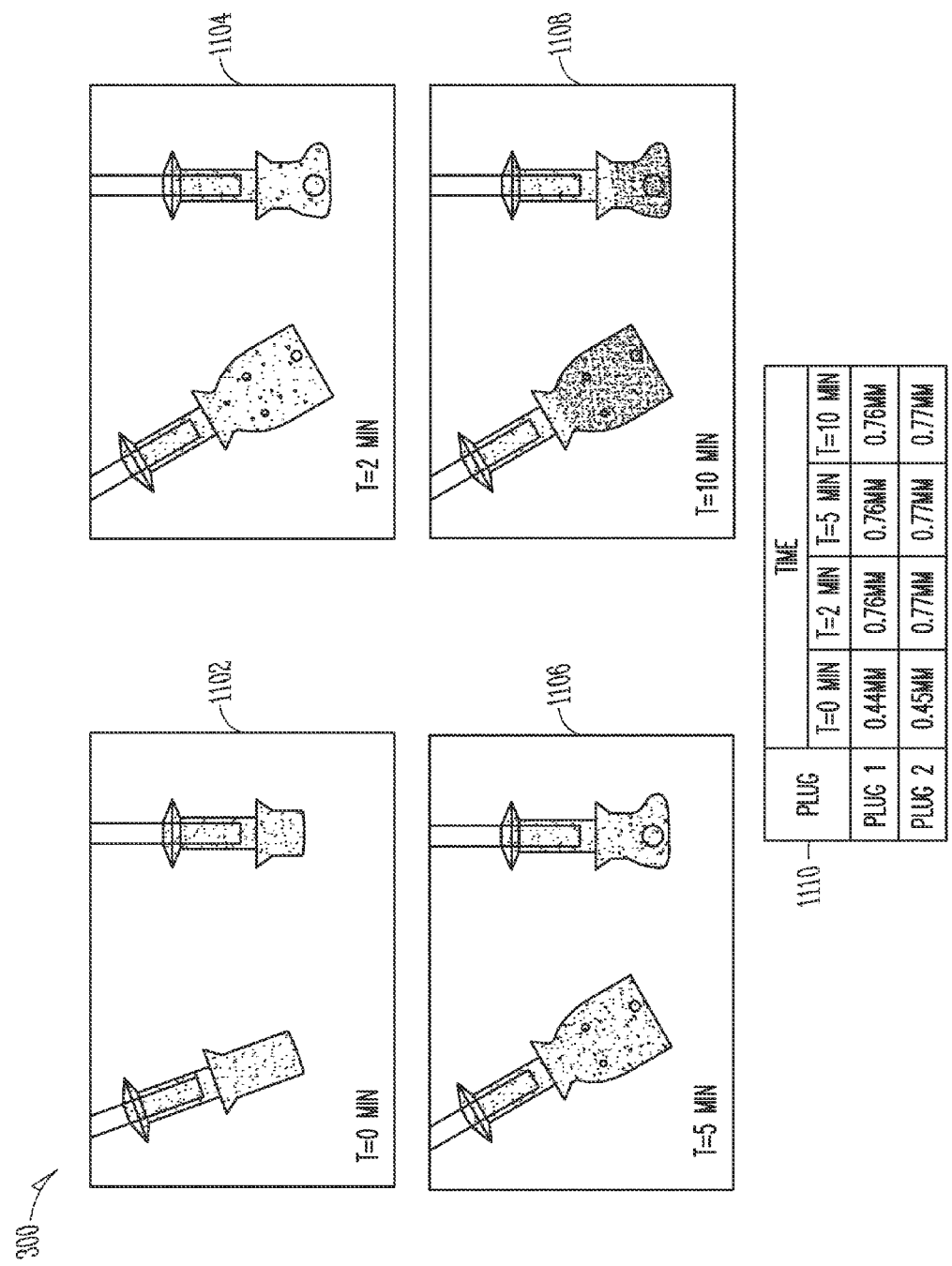

FIG. 11 illustrates two lacrimal implants 300, each comprising a implant body having a first portion and a second portion. In this example, the first portion of the implant body includes a silicone-urethane copolymer, and the second portion of the implant body includes a urethane hydrogel (TG-500®).

The lacrimal implant 300 was tested by soaking in a saline solution and changes to a diameter of the second body portion were measured. At 1102, the implant body, including the first and second portions, are shown at t=0 minutes. At 1104, the implant body, including the first and second portions, are shown at t=2 minutes. At 1106, the implant body, including the first and second portions, are shown at t=5 minutes. At 1108, the implant body, including the first and second portions, are shown at t=10 minutes. Table 1110 shows, among other things that the second portion of the implant body increased in dimensional size from 0.44 millimeters to 0.76 millimeters (a 72% dimensional change) in only 2 minutes.

Experimental Example 4

Figure 12:
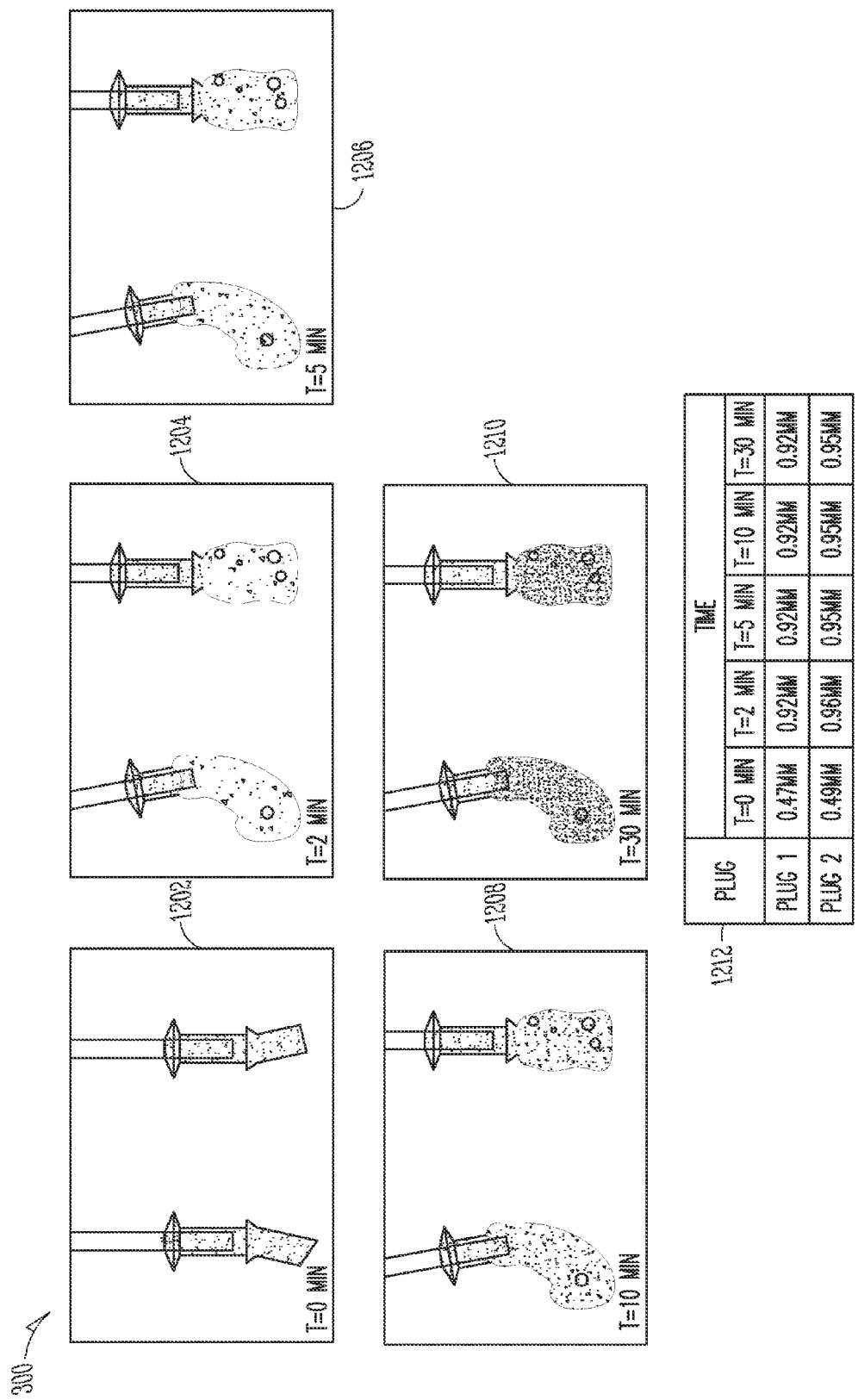

FIG. 12 illustrates two lacrimal implants 300, each comprising a implant body having a first portion and a second portion. In this example, the first portion of the implant body includes a silicone-urethane copolymer, and the second portion of the implant body includes a urethane hydrogel (TG-2000®).

The lacrimal implant 300 was tested by soaking in a saline solution and changes to a diameter of the second body portion were measured. At 1202, the implant body, including the first and second portions, are shown at t=0 minutes. At 1204, the implant body, including the first and second portions, are shown at t=2 minutes. At 1206, the implant body, including the first and second portions, are shown at t=5 minutes. At 1208, the implant body, including the first and second portions, are shown at t=10 minutes. At 1210, the implant body, including the first and second portions, are shown at t=30 minutes. Table 1212 shows, among other things, that the second portion of the implant body increased in dimensional size from 0.47 millimeters to 0.92 millimeters (a 95% dimensional change) in only 2 minutes.

Closing Notes:

Among other things, lacrimal implants and related methods providing secure retention within a lacrimal punctum and canaliculus of an eye are discussed herein. The implant body can include first and second portions, in which the first portion is formed from a polymer and includes a first diameter and the second portion is also formed from a polymer and includes a base member having a second diameter. In various examples, the second diameter of the base member is less than the first diameter of the first body portion. An expandable retention member is coupled at least partially over the base member and is configured to swell via absorption of lacrimal fluid after insertion into the lacrimal punctum. In this way, at least a portion of the expandable retention member can be biased against at least a portion of a lacrimal canaliculus wall to retain an implant position of the lacrimal implant. In various examples, the lacrimal implant can further comprise a drug or other agent supply included in at least one of the first portion or the expandable retention member, such as to provide a sustained release of a therapeutic agent to one or both of an eye or a nasal passage, for instance.

The present lacrimal implants can be securely retained in or near an eye, such as for one or more of successfully blocking the flow of tears from the eye, or providing sustained delivery of a drug or other therapeutic agent to the eye, nasal passage or other portion of the nasolacrimal system. Configuring the lacrimal implant to include an expandable retention member coupled at least partially over a second, smaller diameter portion of the implant body can inhibit the lacrimal implant from inadvertently coming out of an implanted lacrimal punctum and canalicular position, and can be used to at least partially block movement of a fluid through the lacrimal canaliculus. For instance, it may be possible to control the amount of swelling of the expandable retention element to set the lacrimal implant in place, but to prevent over swelling which may tend to push the implant out of the implanted position. In addition, by configuring the expandable retention member to be coupled at least partially over the second, smaller diameter portion of the implant body, adequate adhesion between the expandable retention member (or optionally, an intermediate swellable member) and the implant body is possible via a relatively large surface coupling area.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document, and not claimed priority to, are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable Inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the term "about" is used to refer to an amount that is approximately, nearly, almost, or in the vicinity of being equal to a stated amount.

In this document, the term "proximal" refers to a location relatively closer to a hand of a physician implanting a lacrimal implant into a patient, and the term "distal" refers to a location relatively further from the hand of the physician, particularly during the implanting of the implant into the patient.

In this document, the term "hydrogel" is used to refer to an absorbing or otherwise retaining material (e.g., adsorbing material), such as super-absorbent polymers, hydrocolloids, and water-absorbent hydrophilic polymers, for example. In some examples, the term "hydrogel" refers to super-absorbent polymer particles in a "dry or dehydrated" state, more specifically, particles containing from no water up to an amount of water less than the weight of the particles, such as less than about 5%, by weight, water. In some examples, the term "hydrogel" refers to a super-absorbent polymer in the "dry or dehydrated" state when the hydrogel is not expandable and also refers to its hydrated or expanded state, more specifically, hydrogels that have absorbed at least their weight in water, such as several times their weight in water. As the hydrogel material absorbs fluid, it size can increase and its shape can change to bias against at least a portion of a lacrimal canaliculus ampulla or lacrimal canaliculus wall, for example.

In this document, the term "medicament" is used to refer to an active agent that is suitable for use in medical treatment, such as a medicinal compound or drug.

In this document, the term "active agent" refers to a molecular entity that exerts an effect on a living organism.

In this document, the term "polymer" refers to an organic macromolecule containing one or more repeating units, as is well known in the art. A "copolymer" refers to a polymer in which there are at least two types of repeating units included. A copolymer can be a block copolymer, in which there are segments containing multiple repeating units of one type, bonded to segments containing multiple repeating units of a second type.

In this document, the term "hydrophilic polymer" refers to a polymer that can be wetted by water, i.e., does not have a water-repellant surface. A hydrophilic polymer can absorb water to a small degree, for example about 0-100 wt % of water, but does not greatly swell in volume as does a hydrogel-forming polymer.

In this document, the term "polyurethane" refers to a variety of polymer or copolymer containing repeating units bonded covalently through urethane, i.e., carbamate, bonds, —N—C(O)—O— wherein the N and 0 atoms are attached to an organic radical. The organic radical can be aliphatic, aromatic, or mixed; can contain other functional groups. Each radical, other than the radicals at the ends of the molecular chains, is bonded via two (or more) urethane groups to other radicals. A polyurethane polymer contains only urethane-type groups joining the repeating units. A polyurethane copolymer, such as a polyurethane-silicone copolymer or a polyurethane-carbonate copolymer, contains urethane and other types of groups joining the repeating units, i.e., silicone and carbonate type groups respectively. Examples include Elast-Eon™ by AorTech, a polyurethane-silicone copolymer, Tecoflex® by Lubrizol, an aliphatic flexible polyurethane, Tecothane® by Lubrizol, a thermoplastic polyurethane, and Carbothane® by Lubrizol, a polyurethane/polycarbonate copolymer.

A polyurethane-silicone copolymer contains segments of polyurethane chains and segments of silicone chains, as is well known in the art. An example of a polyurethane-silicone copolymer is "Pursil®", a product of Polymer Technologies Inc., of Berkeley, Calif., described by the manufacturer as a family of aliphatic, thermoplastic silicone polyether urethane copolymers. These polymers are formed by the incorporation of silicone in the polymer backbone together with polyether soft segments, and the use of Surface-Modifying End Groups™ (SME) to terminate the polymer chain. A polyurethane-carbonate copolymer contains urethane segments and carbonate (—O—C(O)O—) segments. An example of a polyurethane-carbonate copolymer is Carbothane TPU® (Lubrizol).

"TG-500" and "TG-2000" are polyurethane hydrogel-forming polymers manufactured by the Thermedics Polymer Products division of Lubrizol Advanced Materials, Inc., of Wilmington, Mass. They are described by the manufacturer as aliphatic, polyether based thermoplastic polyurethanes capable of forming hydrogels. Such hydrogel-forming polymers can absorb greater than 100 wt %, for example up to 500-2000 wt % of water, and consequently swell in physical dimensions.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims.

What is claimed is:

1. A method of delivering a therapeutic agent to an eye, comprising:
   placing a lacrimal implant into a lacrimal canaliculus of a patient, wherein the lacrimal implant comprises:
      a unitary implant body, including first and second portions defining a single longitudinal axis, wherein the unitary body is formed from a substantially non-swelling polymer comprising one or more of a polyurethane polymer, a polyurethane copolymer, or silicone,
      the first portion extending from a proximal end of the implant body, the first portion having a first diameter, wherein the first portion includes a cavity extending inward from the proximal end of the first portion, the cavity having a first supply of a therapeutic agent for release to the eye, and the second portion comprising a distal end portion of the implant body and extending from a distal end of the first portion, the second portion having a second diameter less than the first diameter; and an expandable retention member fully enveloping the second portion of the implant body, the expandable retention member configured to swell via absorption of an aqueous medium after insertion into the lacrimal canaliculus so as to retain the implant body within the lacrimal canaliculus.

2. The method according to claim 1, wherein the substantially non-swelling polymer comprises silicone.

3. The method according to claim 1, wherein the expandable retention member is a hydrogel-forming polyurethane polymer or co-polymer.

4. The method according to claim 1, wherein the first supply includes a solid matrix comprising a mixture of silicone and the first therapeutics agent.

5. The method according to claim 1, further comprising a second supply configured to provide a release of a second therapeutic agent to one or both of a lacrimal canaliculus wall or a nasolacrimal system after contact with an aqueous medium.

6. The method according to claim 1, wherein the second portion further includes one or more arm members extending from an outer surface thereof, and wherein the expandable retention member is coupled over the one or more arm members of the second portion.

7. The method according to claim 1, wherein the therapeutic agent comprises an anti-glaucoma medication, anti-microbial agent, anti-inflammatory agent, a decongestant or an anti-allergic agent.

8. The method according to claim 1, wherein the therapeutic agent comprises a prostaglandin analog.

9. The method according to claim 8, wherein the prostaglandin analog is selected from the group consisting of latanoprost, bimatoprost and travoprost.

10. The method according to claim 1, wherein the therapeutic agent treats glaucoma, post-surgical inflammation, dry eye, post-surgical pain, infection, or allergies.

11. The method according to claim 1, wherein the therapeutic agent further comprises a lubricant or surfactant.

12. The method according to claim 1, wherein the therapeutic agent is present in the first supply as a liquid, solid, solid gel, solid crystalline, solid amorphous, solid particulate or dissolved form.

13. The method according to claim 1, wherein the first supply comprises a matrix selected from acrylate, polyethylene, polyurethane, hydrogel, polyester, or the matrix is selected from a biodegradable polymer.

14. A method of manufacture for a lacrimal implant configured to be inserted into a lacrimal canaliculus of a patient comprising:

forming a unitary implant body, including first and second portions defining a single longitudinal axis, from a substantially non-swelling polymer comprising one or more of a polyurethane polymer, a polyurethane copolymer, or silicone, including forming the first portion extending from a proximal end of the implant body, the first portion having a first diameter, wherein the first portion includes a cavity extending inward from the proximal end of the first portion, forming the second portion comprising a distal end portion of the implant body and extending from a distal end of the first portion, the second portion having a second diameter less than the first diameter;

forming an expandable retention member from a polymer configured to swell via absorption of an aqueous medium after insertion into the lacrimal canaliculus;

coupling the unitary implant body and the expandable retention member wherein the expandable retention member fully envelopes the second portion of the implant body; and, forming a drug supply comprising a therapeutic agent and a matrix for placement in the cavity of the first portion.

15. The method according to claim 14, wherein the substantially non-swelling polymer comprises silicone.

16. The method according to claim 14, wherein the therapeutic agent comprises an anti-glaucoma medication, anti-microbial agent, anti-inflammatory agent, a decongestant or an anti-allergic agent.

17. The method according to claim 14, wherein the therapeutic agent comprises a prostaglandin analog.

18. The method according to claim 17, wherein the prostaglandin analog is selected from the group consisting of latanoprost, bimatoprost and travoprost.

19. The method according to claim 14, wherein the matrix is selected from silicone, acrylate, polyethylene, polyurethane, hydrogel, polyester, or the matrix is selected from a biodegradable polymer.

* * * * *